US012390275B2

(12) United States Patent
Tanzer et al.

(10) Patent No.: US 12,390,275 B2
(45) Date of Patent: Aug. 19, 2025

(54) AUGMENTED/MIXED REALITY SYSTEM AND METHOD FOR ORTHOPAEDIC ARTHROPLASTY

(71) Applicants: Michael Tanzer, Hampstead (CA); Adam Hart, Outremont (CA); Bardia Barimani, Verdun (CA); Carl Laverdiere, Montreal (CA)

(72) Inventors: Michael Tanzer, Hampstead (CA); Adam Hart, Outremont (CA); Bardia Barimani, Verdun (CA); Carl Laverdiere, Montreal (CA)

( * ) Notice: Subject to any disclaimer, the term of this patent is extended or adjusted under 35 U.S.C. 154(b) by 257 days.

(21) Appl. No.: 17/860,471

(22) Filed: Jul. 8, 2022

(65) Prior Publication Data

US 2023/0018541 A1    Jan. 19, 2023

Related U.S. Application Data

(60) Provisional application No. 63/219,521, filed on Jul. 8, 2021.

(51) Int. Cl.
*A61B 34/10*    (2016.01)
*A61B 34/20*    (2016.01)
(Continued)

(52) U.S. Cl.
CPC ............. *A61B 34/10* (2016.02); *A61B 34/20* (2016.02); *A61B 90/36* (2016.02); *A61B 90/39* (2016.02);
(Continued)

(58) Field of Classification Search
CPC ......... A61B 34/10; A61B 34/20; A61B 90/36; A61B 90/39; G06F 3/011; G06F 3/017
See application file for complete search history.

(56) References Cited

U.S. PATENT DOCUMENTS 9,138,319 B2    9/2015    Fanson et al.
9,861,446 B2    1/2018    Lang
(Continued)

FOREIGN PATENT DOCUMENTS

WO    2020123701 A1    6/2020
WO    2021007418 A2    1/2021

OTHER PUBLICATIONS

Seagrave KG, Troelsen A, Malchau H, Husted H, Gromov K. Acetabular cup position and risk of dislocation in primary total hip arthroplasty. Acta Orthop. 2017;88(1):10-7.
(Continued)

*Primary Examiner* — Dixomara Vargas
(74) *Attorney, Agent, or Firm* — Jacob M. Ward; Ward Law Office LLC

(57) ABSTRACT

Augmented and/or mixed reality systems for performing various types of arthroplasty are provided, along with methods of performing various types of arthroplasty using such augmented reality systems. More particularly, the augmented and/or mixed reality system and method is used to achieve accurate bone preparation, implant placement and orientation, and biomechanical restoration in orthopaedic arthroplasty procedures. Preparation, implantation, and adjustment of arthroplasty surgical sites, prosthetic components, and tailoring and positioning of installed prosthetic components can be guided using augmented reality overlays, projections, or combined imaging of a surgeon's real-world view.

20 Claims, 12 Drawing Sheets

(51) Int. Cl.
*A61B 90/00* (2016.01)
*G06F 3/01* (2006.01)

(52) U.S. Cl.
CPC .............. *G06F 3/011* (2013.01); *G06F 3/017* (2013.01); *A61B 2034/104* (2016.02); *A61B 2034/105* (2016.02); *A61B 2034/108* (2016.02); *A61B 2034/2065* (2016.02); *A61B 2034/2068* (2016.02); *A61B 2090/365* (2016.02); *A61B 2090/3916* (2016.02); *A61B 2090/3983* (2016.02); *A61B 2560/0271* (2013.01)

(56) References Cited

U.S. PATENT DOCUMENTS

| | | |
|---|---|---|
| 9,980,780 B2 | 5/2018 | Lang |
| 10,092,361 B2 | 10/2018 | Ferro et al. |
| 10,117,748 B2 | 11/2018 | Fanson et al. |
| 10,154,239 B2 | 12/2018 | Casas |
| 10,231,786 B2 | 3/2019 | Ferro et al. |
| 10,278,777 B1 | 5/2019 | Lang |
| 10,292,768 B2 | 5/2019 | Lang |
| 10,368,947 B2 | 8/2019 | Lang |
| 10,405,927 B1 | 9/2019 | Lang |
| 10,449,004 B2 | 10/2019 | Ferro et al. |
| 10,603,113 B2 | 3/2020 | Lang |
| 10,603,133 B2 | 3/2020 | Wang et al. |
| 10,973,590 B2 | 4/2021 | Boddington et al. |
| 2017/0312031 A1* | 11/2017 | Amanatullah ......... A61B 34/10 |
| 2017/0312032 A1* | 11/2017 | Amanatullah ......... G09B 23/30 |
| 2018/0303563 A1 | 10/2018 | West et al. |
| 2021/0121237 A1 | 4/2021 | Fanson et al. |
| 2021/0161612 A1 | 6/2021 | Black et al. |
| 2021/0169587 A1 | 6/2021 | Martin, III et al. |
| 2021/0177522 A1 | 6/2021 | Boddington et al. |
| 2022/0192844 A1* | 6/2022 | Thompson ............ A61B 34/20 |
| 2023/0019543 A1* | 1/2023 | Nikou .................... A61B 8/461 |
| 2024/0058064 A1* | 2/2024 | Weiser .................. A61B 34/20 |

OTHER PUBLICATIONS

Archbold HA, Mockford B, Molloy D, McConway J, Ogonda L, Beverland D. "The transverse acetabular ligament: an aid to orientation of the acetabular component during primary total hip replacement: a preliminary study of 1000 cases investigating postoperative stability." J Bone Joint Surg Br. 2006; 88(7):883-6.

Zhang et al., Towards an integrated high-fidelity linkage representation of the human skeletal system based on surface measurement, International Journal of Industrial Ergonomics, 2004, pp. 215-227, 33, Elsevier B.V., Urbana, IL, USA.

Zhang et al., A Normative Database of Thumb Circumduction In Vivo: Center of Rotation and Range of Motion, Human Factors, vol. 47, No. 3, Fall 2005, pp. 550-561, Human Factors and Ergonomics Society, Urbana, IL, USA.

Biggs et al., A three-dimensional kinematic model of the human long finger and the muscles that actuate it, Medical Engineering & Physics 21 (1999) 625-639, Elsevier Science Ltd., Salt Lake City, UT, USA.

Written Opinion of the International Searching Authority dated Oct. 6, 2022.

* cited by examiner

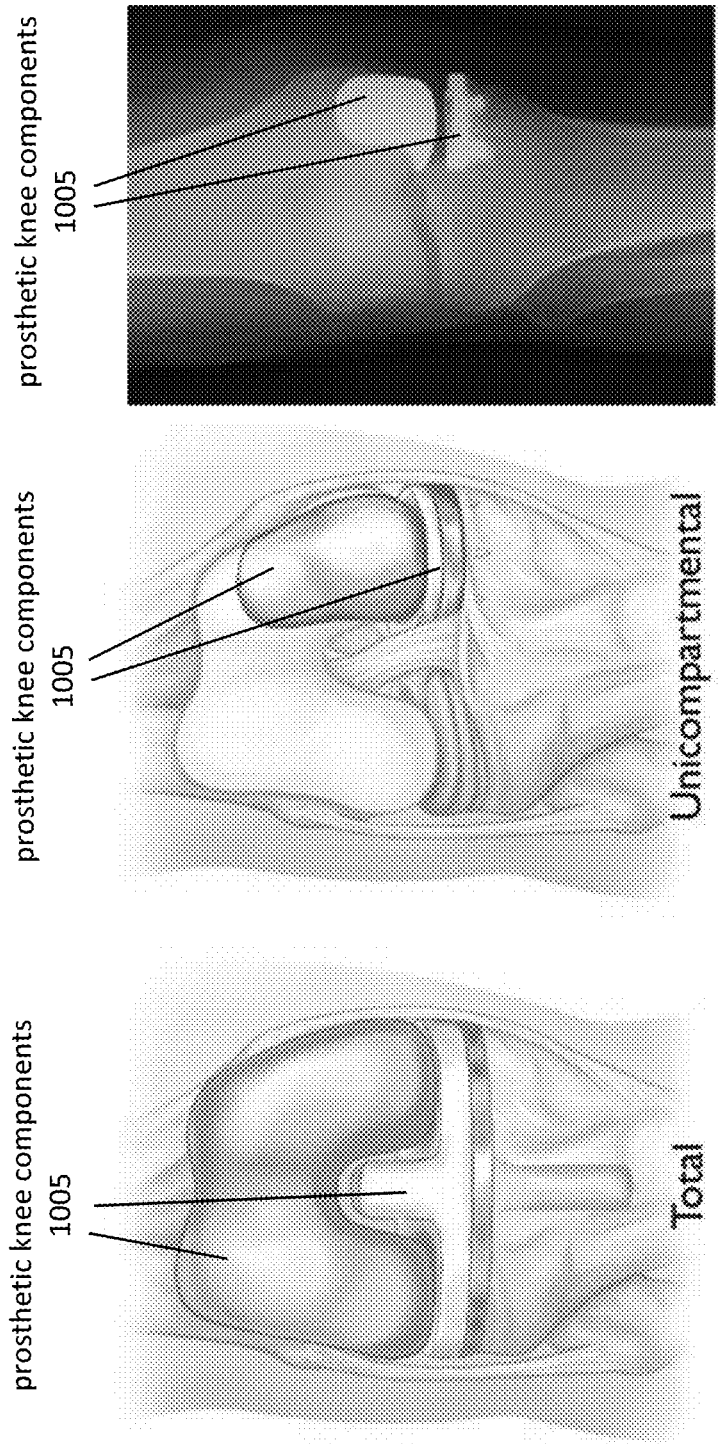

AUGMENTED/MIXED REALITY SYSTEM AND METHOD FOR ORTHOPAEDIC ARTHROPLASTY

CROSS-REFERENCE TO RELATED APPLICATIONS

This application claims the benefit of U.S. Provisional Application No. 63/219,521, filed on Jul. 8, 2021. The entire disclosure of the above application is incorporated herein by reference.

FIELD

The present technology relates to ways of performing arthroplasty using augmented reality, including where the arthroplasty can be performed freehand without the necessity of a robot and/or traditional navigation markers in preparation of a joint and implantation of one or more prosthetic components.

INTRODUCTION

This section provides background information related to the present disclosure which is not necessarily prior art.

Arthroplasty generally includes orthopedic surgical procedures where an articular surface of a musculoskeletal joint is replaced, remodeled, partially or completely resurfaced, or realigned by osteotomy or some other procedure. Various types of arthroplasty can be performed to relieve pain and/or restore function to a joint after disease or damage, for example, resulting from arthritis or trauma. Particular examples of musculoskeletal joints subject to arthroplastic procedures include the hip, knee, ankle, elbow, and shoulder.

Hip arthroplasty is a surgical procedure where a hip joint can be replaced or resurfaced by a prosthetic implant. Hip replacement surgery can be conducted to relieve arthritis pain, can be part of reconstruction following trauma, such as a hip fracture, or for numerous other etiologies. Total hip arthroplasty (THA), also referred to as total hip replacement, can include replacement of both the acetabulum and the femoral head, whereas hemiarthroplasty can include replacement of the femoral head. Hip resurfacing can include the capping of the joint with one or more prosthetic implants.

Knee arthroplasty, or knee replacement, is a surgical procedure that includes complete or partial replacement of the surfaces of the knee joint to relieve pain and disability. Knee replacement can be performed for osteoarthritis, as well as for numerous other knee conditions or diseases, such as rheumatoid arthritis and psoriatic arthritis. Knee replacement surgery can be performed as a partial or a total knee replacement. Replacement of diseased or damaged joint surfaces of the knee can be performed using metal and/or plastic components shaped to allow continued motion of the knee.

Surgical joint repair procedures can involve repair and/or replacement of a damaged or diseased joint with a prosthetic that is implanted into one or more bones of the patient. A desirable outcome can be dependent upon proper selection of a prosthetic that is appropriately sized and shaped, along with proper positioning and orientation of that prosthetic during the surgical procedure. To assist with positioning and orientation, the surgical procedure can include the use of surgical instruments to control the shaping and orientation of one or more surfaces of bone, which can include cutting, milling, rotatory filing or drilling of all or part of the bone to accept the prosthetic.

Various virtual visualization tools are becoming available to surgeons, where such tools use three-dimensional modelling of bone shapes to facilitate preoperative planning and intraoperative guidance for joint repairs and replacements. These tools can assist surgeons with surgical design and/or guidance and can facilitate the selection, placement, and orientation of implants that closely match the respective anatomy, including adjustments to a particular patient's anatomy and pathology to improve surgical outcomes by customizing a surgical plan for each patient. Accordingly, there is a need to optimize arthroplasty by providing surgical guidance to procedure steps and operations to ensure proper preparation and implantation of prosthetics that are used to repair or replace articular surfaces of a musculoskeletal joint.

SUMMARY

In concordance with the instant disclosure, augmented reality systems for performing various types of arthroplasty are provided, along with methods of performing various types of arthroplasty using such augmented reality systems, as shown and described herein.

The present technology provides several advantageous aspects that can function in concert to improve arthroplasty, especially with respect to real-time performance of joint preparation and implant component installation during surgery. The combined functionalities of the present systems and processes can minimize the time required for surgical steps, can optimize preparation of bone surfaces and implant placement, can optimize restoration of the biomechanics of the joint, and can furthermore provide real-time adaptable models to allow an operator, such as an orthopedic surgeon, to tailor the arthroplasty to a particular patient based upon the particular anatomy of the patient, one or more optimized models, as well as hybrid approaches taking into account both the particular anatomy of the patient and one or more optimized models.

Various selections of these advantageous aspects can be employed, depending on a particular arthroplasty procedure and a desired level of augmented reality guidance. Certain embodiments include where head mounted augmented reality displays are employed, where augmented reality can be presented to an operator as the operator looks about a surgical theater. It is also possible to employ non-head mounted augmented reality displays, including screens, windows, and projections that are viewable by the operator adjacent to a surgical site or projected thereon. Screens and windows can also be positioned to allow the operator to view at least a portion of the surgical site therethrough, either in reality where a portion of the screen or window may be transparent and work in conjunction with one or more holographic images to provide a mixed reality view, or where the screen or window display a representation of what lies behind the screen or window, including real-time movement and updates of what is occurring in a region beyond the screen or window, including any augmented representations. For example, certain projection mapping components can be employed. Likewise, certain contact lens displays can be used.

Certain embodiments of the present technology can employ constant optimization based on one or more types of feedback. For example, tracking modalities can be used to update the surgical site, anatomical components, surgical tools, and/or the surgeon's hands or gloves. In this way, registration of one or more landmarks used to correlate augmented and/or mixed reality annotations can be continuously updated or "nudged" during a step or procedure without the need to re-register a surgical site or feature. Augmented reality, for example, can provide one or more virtual objects into a real image or scene. Certain augmented reality modalities can register the virtual object(s) in alignment with the real image or scene using various techniques. Often, one or more changes in the real image or scene may necessitate re-registration, or correction of the alignment of the virtual world with the real one. Embodiments of the present technology, however, only need to register once. A real time imaging modality can be created to obviate the need to re-register following a change in features, completion of one or more surgical steps, and/or anatomical movement, for example. Particular advantages relate to the open nature of arthroplasty surgical procedures, where the present technology obviates any need to re-register due to motion or displacement of the patient. This can provide an advantage in testing and/or projecting the articulation of a joint before, during, and after various corrections and/or implants are in place. Once the anatomy is registered, landmarks, features, or markers can be identified or placed within the surgical site, not external thereto, so that the augmented and/or mixed reality can continuously determine if the anatomy has moved and hence account for such movement.

The present technology can employ optical tracking, but optical tracking methods may not be ideal in certain surgical environments, for example, where an operating room includes equipment and other operators or individuals present around an operating table, which can block the line-of-sight a given operator. The present technology can therefore include or rely upon markerless tracking modalities, including tracking technologies, such as electromagnetic tracking, that does not interfere with operating room equipment.

In certain embodiments, the present technology can be adapted to address what is seen by the operator(s) and associated personnel around the patient and operating table. To this point, the present technology can provide what can be described as a "shared view," where all participants can see what is viewed by the primary operator (e.g., primary surgeon). This aspect can be important as the other personnel in the operating theater are all standing in different locations and can be facing different directions, and hence each can have a different perspective of a surgical site. The present technology therefore can provide a representation to selected or all participants that represents the same view as the primary operator/surgeon who is likely to be only one standing in the ideal location for performing the step or procedure. The "shared view" image can therefore be fixed to the ideal location, so when the primary operator turns his/her head, the augmented image is fixed with respect to the patient's anatomy; e.g., mixed reality. As well, surgeries can take hours and the surgeons tend to look around at the nursing set up, other areas of the operating room, etc. and not always at the surgical site. The mixed augmented reality can therefore be selectively turned off by the operator in various ways; e.g., by voice, command, by hand gesture, or even by turning his/her head more than a specified amount such as 45 degrees of rotation. For example, when the operator looks to the side to get an instrument, etc. from a nurse or surgical technician, the image can automatically turn off if it is on a mode to do so. This can be personalized for individual operators.

The present technology is configured to employ intraoperative registration without the use of any preoperative images. However, embodiments can also incorporate preoperative and/or intraoperative images or imaging modalities. As such, registration employs anatomical landmarks in lieu of or in addition to preoperative imaging, like navigation, to create the augmented/mixed reality image. For example, intraoperative registration can include identification of one or more specific bone and/or soft tissue landmarks. This can generate an image, use image matching/recognition including the use of artificial intelligence, and/or create the image from an anatomical atlas; e.g., create a virtual joint by artificial intelligence based upon an atlas or database that most closely matches the patient's anatomy by a predetermined threshold.

Registration can be performed for all areas of the surgical site that are visible or palpable. For the areas not visible in the surgical site, registration can be performed using palpation of the anatomy or by using other modalities, such as ultrasound. Registration of visible and nonvisible points in this way can elucidate location and mapping of a bone of interest and/or an axis of alignment. Imaging the bone outside of the visible operative site can allow the operator to prepare the bone without the risk of perforation or other undesired modifications thereto. For example, in a direct anterior approach of the hip joint, the operator can broach the femur more safely by knowing its position, and canal size by ultrasound, thereby seating a correctly sized broach and implant in an optimized alignment. In the knee, for example, it can ensure that the implant is perpendicular to the long access of the tibia, amongst other preferred metrics. Ultrasound registration can also allow for a more minimally invasive incision and operation since the bone can be identified outside the surgical site to create a larger image, including an augmented reality projection or hologram of portions of the bone that are not visible, or even the entire subject bone, in certain embodiments. Registration including ultrasound can also identify a depth of bone and a width of bone to optimize selection of implant components; e.g., ensure the appropriate length of screw, canal filling implant, etc. Ultrasound can further be used as a soft tissue sensor to determine a balance of the soft tissues in a region of interest. In a knee, it can determine flexion and extension gaps so as to indicate if further soft tissue releases are required, if the implant size should be changed, or its orientation modified, for example. This can be done in conjunction with artificial intelligence that can select and form an image based upon data (e.g., bone atlas) as well as predetermined mapping thresholds.

In certain embodiments, artificial intelligence can be used in conjunction with augmented/mixed reality. Execution of artificial intelligence applications to augmented reality processing, displays, and image determinations based upon registration and real-time updated registration can be voice or gesture activated. The artificial intelligence component can be used preoperatively or intraoperatively. Preoperatively, like in robotics, artificial intelligence can be used to determine or predict the size, location, and orientation of implant components, especially with respect to interactions there between in optimizing movement axes. Preoperatively, artificial intelligence can recognize hip impingement of a planned surgery, optimal implant size, orientation and position to maximize movement and minimize bone loss, for example. These details and determinations can then be used intraoperatively by the artificial intelligence in generating the augmented/mixed reality to provide markers for desired location(s) and orientation(s) of the implant(s). Artificial intelligence can also determine, indicate, and display a depth of bone removal using the augmented reality display. Intraoperatively, constant optimization of the registration can indicate if implant components are in a desired position, or whether position and/or orientation thereof need to be modified. For example, if implant positioning results in leg shortening or loss of offset, the artificial intelligence can identify such to the operator and provide optional measurements and/or guidance with respect to one or more corrective maneuvers to correct undesired outcomes; e.g., such as an increase in head length. As well, after measuring knee soft tissue kinematics, by ultrasound or sensor, the artificial intelligence can update a surgical step or plan to adjust knee implant size and or position as needed. Artificial intelligence can therefore provide feedback and display options to recreate desired kinematics and biomechanics of the subject joint, including where the artificial intelligence can do so based upon using real-time updates or "nudges" of the registration to optimize predictive dynamics using bone preparation measurements and/or implant fitment parameters.

An addition to the use of artificial intelligence, the present technology can provide the ability to touch the control panel of a robot, navigation system, and/or analytic system using a virtual control panel. This functionality eliminates the need for the operator to turn his/her attention from the surgical site and perform such an action on a sterile panel or have another participant in the room executing the desired commands of the operator/surgeon.

Aspects of the present technology can further include registration of the surgical site akin to how the site is viewed by an operator or surgeon. For example, the operator (e.g., surgeon) is provided with a visual representation of an operative region of interest. If the patient moves, the operator can recognize the deviation. The entire surgical field does not have to be viewed to recognize movement or deviation. Likewise, movement or deviation of part of the surgical field can still be determined with respect to one or more areas of the surgical field that have changed as a result of the surgical procedure; e.g., bone reaming or a cut where bone is removed. The operator uses fixed visual cues that are not going to be modified by the surgery to orient the anatomy. The same operation can occur with the augmented/mixed reality system. In particular, registration can include visual cues; e.g., a head mounted display images limited portions of the patient's anatomy, such as two or more points of the anatomy are recognized by the system. In the acetabulum, for example, the system can recognize the transverse acetabular ligament, a point on the posterior column, and the anterior column. Recognition and registration in this manner can replace the markers used in other systems with "reference points" that are anatomically based. These anatomical reference points are hence static points used for registration. Since they are static, there are no issues or problems resulting from movement of the operator's head when wearing a head mounted display. One or more cameras in the head mounted display can continuously take one or more new images, where the new image(s) can be compared to one or more previous images so that the augmented/mixed reality can be reoriented. The system therefore can operate in a markerless fashion and use comparative images of surface topography to act as the reference points.

Certain embodiments of the present technology can further include where other operators or participants in an arthroplasty can provide one or more images or projections to the primary operator performing the procedure. Such additional operators or participants can include individuals that are not necessarily in the operating theater or even the same facility. In this way, one or more remote parties can provide guidance to the operator at various steps in a surgical procedure. For example, the system can be configured to allow for a "virtual presence" of one or more additional individuals. This functionality can allow other surgeons to assist the operator remotely by using a virtual hand or by annotation of the augmented/mixed reality. Such capability can also be used by various surgical representatives that do not need to be in the actual operating room, as well as for teaching and telemedicine applications.

In certain embodiments, the present technology provides various methods of performing arthroplasty on a surgical site of a patient by an operator using an augmented reality system. Such methods can employ a system including an imaging device, a display device, and a computer system. The imaging device can be configured to acquire a first image of the surgical site and the display device can be configured to display an augmented reality depiction of the surgical site. The computer system can have a processor and a memory, where the computer system can be in communication with the imaging device and the display device. The memory can include various operational functionalities, which can be defined or compartmentalized as one or more modules directed toward certain operations. For example, the memory can include tangible, non-transitory, machine-readable instructions, which can be used to define various modules. The memory, in particular, can include a registration module configured to correlate a predetermined surgical plan with the first image to generate the augmented reality depiction of the surgical site using the first image. The present methods can include various actions, including where the operator views the augmented reality depiction of the surgical site using the display device. The operator can prepare a portion of the surgical site using a surgical instrument guided by the augmented reality depiction to form a prepared site. The operator can then position a prosthetic implant at the prepared site to form a positioned implant.

In certain embodiments, the present technology provides various augmented reality systems for performing arthroplasty on a surgical site of a patient by an operator. Such systems can include an imaging device, a display device, and a computer system having a processor and memory. The imaging device can be configured to acquire and update a first image of the surgical site in real time. The display device can be configured to display an augmented reality depiction of the surgical site. The computer system can be in communication with the imaging device and the display device. The memory of the computer system can include one or more of a registration module, an image module, a predictive module, a positioning module, a tracking module, and a modification module. The registration module can be configured to correlate a predetermined surgical plan with the first image to generate the augmented reality depiction of the surgical site using the first image. The image module can include a preexisting image of the surgical site, where the registration module can be configured to correlate the predetermined surgical plan with the first image and the preexisting image to generate the augmented reality depiction of the surgical site using the first image. The predictive module can be configured to correlate a predictive image based upon the predetermined surgical plan with the first image to generate the augmented reality depiction of the surgical site using the first image. The positioning module can be configured to correlate the positioned implant at the prepared site with the predetermined surgical plan and determine an implant deviation. The tracking module can be configured to determine a track of the surgical instrument using the first image, where the registration module can be further configured to generate the augmented reality depiction of the surgical site including a predetermined approach of the surgical instrument to the surgical site based upon the track of the surgical instrument determined using the first image by the tracking module. The modification module can be configured to modify the predetermined surgical plan, where the display device can be further configured to display an augmented reality depiction including a control panel configured to respond to a gesture of the operator to communicate with the modification module and allow the operator to modify the predetermined surgical plan. The computer system can be in communication with a remote system, where the remote system can be configured to access the modification module, thereby allowing a remote operator to modify the predetermined surgical plan.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 10A-10C show schematic views of a total knee arthroplasty (TKA), a unicompartmental knee arthroplasty (UKA), and a radiographic image of a UKA, respectively.

DETAILED DESCRIPTION

Figure 1:
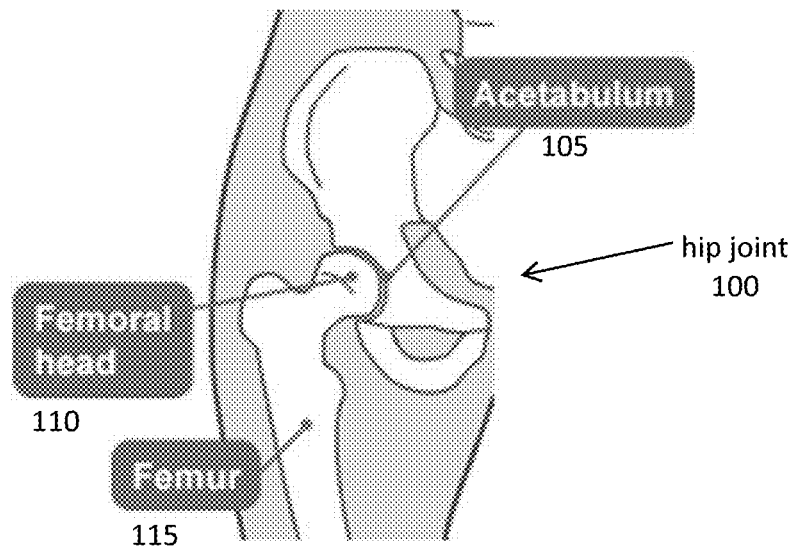
FIG. 1 shows a schematic view of a hip joint, depicting an acetabulum of a pelvis and a femoral head of a femur.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. Regarding methods disclosed, the order of the steps presented is exemplary in nature, and thus, the order of the steps can be different in various embodiments, including where certain steps can be simultaneously performed, unless expressly stated otherwise. "A" and "an" as used herein indicate "at least one" of the item is present; a plurality of such items may be present, when possible. Except where otherwise expressly indicated, all numerical quantities in this description are to be understood as modified by the word "about" and all geometric and spatial descriptors are to be understood as modified by the word "substantially" in describing the broadest scope of the technology. "About" when applied to numerical values indicates that the calculation or the measurement allows some slight imprecision in the value (with some approach to exactness in the value; approximately or reasonably close to the value; nearly). If, for some reason, the imprecision provided by "about" and/or "substantially" is not otherwise understood in the art with this ordinary meaning, then "about" and/or "substantially" as used herein indicates at least variations that may arise from ordinary methods of measuring or using such parameters.

All documents, including patents, patent applications, and scientific literature cited in this detailed description are incorporated herein by reference, unless otherwise expressly indicated. Where any conflict or ambiguity may exist between a document incorporated by reference and this detailed description, the present detailed description controls.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components, or process steps, the present technology also specifically includes embodiments consisting of, or consisting essentially of, such materials, components, or process steps excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, disclosures of ranges are, unless specified otherwise, inclusive of endpoints and include all distinct values and further divided ranges within the entire range. Thus, for example, a range of "from A to B" or "from about A to about B" is inclusive of A and of B. Disclosure of values and ranges of values for specific parameters (such as amounts, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, 3-9, and so on.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

As used herein, the term "tracking system" and "tracking module" refers to something used to observe one or more objects undergoing motion and supply a timely ordered sequence of tracking data (e.g., location data, orientation data, or the like) in a tracking coordinate system for further processing. As an example, the tracking system can be an electromagnetic tracking system that can observe a surgical instrument equipped with a sensor-coil as the surgical instrument moves relative to a patient's body.

As used herein, the term "tracking data" refers to information recorded by the tracking system related to an observation of one or more objects (e.g., a surgical instrument, prosthetic implant, etc.) undergoing motion.

As used herein, the term "tracking coordinate system" refers to a three-dimensional (3D) Cartesian coordinate system that uses one or more numbers to determine the position of points or other geometric elements unique to the particular tracking system. For example, the tracking coordinate system can be rotated, scaled, or the like, from a standard 3D Cartesian coordinate system.

As used herein, the term "head mounted display" refers to a display device, configured to be worn on the head, that has one or more display optics (including lenses) in front of one or more eyes. These terms can be referred to even more generally by the term "augmented reality system," although it should be appreciated that the term "augmented reality system" is not limited to display devices configured to be worn on the head. In some instances, the head-mounted device can also include a non-transitory memory and a processing unit. Example of suitable head-mounted devices include various versions of the Microsoft HoloLens® mixed reality smart glasses.

As used herein, the terms "imaging device" or the like refers to technology that acquires and creates a visual representation of a portion of a patient's body, such as a surgical site. For example, the imaging device can include one or more imaging devices and one or more imaging modalities. Certain embodiments include where the imaging device includes an optical camera system configured to capture one or more images, including real time capture of images continuously as video, in the visible spectrum. Other imaging devices can include capture of other portions of the electromagnetic spectrum, including infrared and ultraviolet portions. The imaging device can include additional imaging modalities such as a computed tomography (CT) system, a fluoroscopy system, a magnetic resonance imaging (MRI) system, an ultrasound (US) system, or the like. In conjunction with the registration module, the imaging device can provide multiple types of images that can be used to form one or more various types of composite images, where the composite image can be used in generating an augmented reality depiction of the surgical site.

As used herein, the terms "coordinate system" or "augmented realty system coordinate system" refer to a 3D Cartesian coordinate system that uses one or more numbers to determine the position of points or other geometric elements unique to the particular augmented reality system or image acquisition system to which it pertains. For example, a head mounted display coordinate system can be rotated, scaled, or the like, from a standard 3D Cartesian coordinate system.

As used herein, the terms "image" or "image data" refers to information recorded by the imaging device related to an observation of the interior of the patient's body. The image can include information acquired and stored or translated to a three dimensional coordinate system. For example, the "image" or "image data" can include processed two-dimensional or three-dimensional images or models such as tomographic images; e.g., represented by data formatted according to the Digital Imaging and Communications in Medicine (DICOM) standard or other relevant imaging standards.

As used herein, the term "real time" refers to the actual time during which a process or event occurs. In other words, a real time event is done live (within milliseconds so that results are available immediately as feedback). For example, a real time event can be represented within 100 milliseconds of the event occurring.

As used herein, the term "registration" refers to steps of transforming tracking data and body image data to a common coordinate system and creating an augmented or mixed reality display of images and information relative to a body of a physical patient during a procedure, for example, as described in U.S. Patent Application Publication No. 2018/0303563 to West et al., U.S. patent application Ser. No. 17/110,991 to Black et al., and U.S. patent application Ser. No. 17/117,841 to Martin III et al., the entire disclosures of which are incorporated herein by reference.

The present technology utilizes augmented reality, which can include utilizing mixed reality, to achieve accurate bone preparation, implant placement and orientation, and biomechanical restoration in orthopedic arthroplasty procedures. Preparation, implantation, and adjustment of arthroplasty surgical sites, prosthetic components, and tailoring and positioning of installed prosthetic components can be guided using augmented and/or mixed reality overlays, projections, or combined imaging of a surgeon's real-world view. Various types of displays, including, but not limited to mixed reality goggles or glasses, can permit a surgeon to effect an arthroplasty without robotics and/or other computer-assisted navigational aids. Presently, preparation of musculoskeletal joints for implantation of various prosthetics can require use of an automated process, which can include use of a robot (e.g., Mako robot, Stryker, Kalamazoo, MI) and/or computer-assisted navigation (e.g., infrared marker pins). Using augmented and/or mixed reality, a surgeon can achieve similar intraoperative outcomes without having to employ a robot or computer-assisted navigation. The present technology can be applied to various types of arthroplasty, including particular types of orthopedic arthroplasties relating to the hip, knee, shoulder, elbow, and ankle.

The present technology includes the use of augmented reality using mixed reality smart glasses (e.g., Microsoft HoloLens 2) or other displays and/or devices to overlay a surgical plan, including superimposing aspects of the surgical plan directly onto the patient during the procedure in real time, during a joint arthroplasty (e.g., total hip arthroplasty (THA), partial knee arthroplasty (uni TKA), total knee arthroplasty, etc.) in order to optimize bone preparation and position of one or more implant components as well as optimize the joint biomechanics and kinematics. It is accordingly possible to use the present technology to obtain many of the same benefits of robotic surgery, without the added cost, and in a simplified and time efficient manner. Systems and methods provided herein can use imageless and pinless navigation (without pins external to the surgical field) modes to provide intraoperative guidance to the surgeon. As per robotic surgical systems, the present technology can display an optimal orientation of bony preparations, one or more specific bone cuts and depths of bone removal, as well as optimal implant placement through holographic features. The surgeon is consequently able to plan to place the implants anatomically, or in modified, but planned alignment.

In certain embodiments, the present technology can employ augmented reality using mixed reality smart glasses (e.g., Microsoft HoloLens 2) or other displays and/or devices to overlay a surgical plan in real time during a procedure to facilitate bone preparation and implant positioning in preparing a musculoskeletal joint site and fitting of one or more prosthetic components. Depth sensing cameras can be used, whilst combining surface mapping and 3D object tracking, to guide the surgeon through one or more steps of a given procedure, e.g., bone preparation orientation, bone reaming, bone cuts, implant positioning, etc. For example, quick response (QR) codes can be located on various tools, such as on a reamer, milling device, rotatory file, and/or a saw, where the system can visually highlight to the surgeon the bone and location that is necessary to be removed, prepped, and/or resurfaced by the cutting tool—e.g., in both sagittal and coronal planes—as well as the proper orientation of the bone resection in real time. It is therefore possible for the surgeon to perform bone removal by freehand using a visually highlighted region, as described, or by referencing and using the highlighted area that needs to be removed as a marker to attach a guide, which can then be used to accurately cut, prep, or resurface the bone. This can accordingly limit any intraoperative error of over/under reaming as well as minimize erroneous cuts. Leveraging the power of augmented reality and/or mixed reality, the present technology can provide imageless and pinless navigation (without pins external to the surgical field), streamline a surgical workflow, as well as reduce a cost per procedure.

In certain embodiments, the present technology can be used without any preoperative and/or intraoperative imaging. However, it is possible to incorporate preoperative and/or intraoperative imaging, as well. For example, various anatomic landmarks can be used during the procedure for guidance and generation of mixed reality imaging, where no preoperative imaging is necessary. Although, it is still possible for the system to take advantage of preoperative imaging data, such as CT scan or MRI data, in highlighting, determining, and/or adjusting an area that needs to cut, prep, or resurfaced for prosthetic implantation. Embodiments also include where the mixed reality can provide guidance using pinless markers, but the system and methods provided herein can also incorporate intraoperative markers within the surgical field as may be needed in certain instances.

Aspects of the present technology are now presented in the context of several arthroplasty examples.

Total hip arthroplasty involves the hip joint, which is a ball and socket joint formed by articulation between the femoral head (top of the thigh bone) and the acetabulum (pelvis). During total hip arthroplasty (THA) both parts are replaced. Correct position of the components directly correlates with success of the implant. Implantation of the acetabular cup can follow desired positioning and guidance known in the art, including aspects as detailed by Seagrave K G, Troelsen A, Malchau H, Husted H, Gromov K. Acetabular cup position and risk of dislocation in primary total hip arthroplasty. Acta Orthop. 2017; 88(1):10-7. The present technology can therefore be applied to positioning of the acetabular cup. This can include a registration method and technique that can include preoperative and/or perioperative image processing, which can include the use of pinless markers or pins, including and/or embodying various anatomical landmarks, within the surgical field.

Various acetabulum registration landmarks can be used. Surface mapping of the acetabulum can include use of well-known anatomical landmarks that are visible with all the commonly used THA surgical approaches, e.g., posterior, direct lateral, and direct anterior. Examples of landmarks can include one or more of each of: (1) soft tissue (e.g., transverse acetabular ligament (TAL), ligamentum teres, and/or labrum and (2) bone (e.g., acetabular notch, anterior/posterior rim of the acetabulum, and/or centre of acetabular roof), and (3) extraarticular landmarks of the pelvis (e.g., pubis, anterior superior iliac spines).

With respect to anatomy of the acetabulum, aspects of anatomical positions, locations, and landmarks can include those disclosed by Archbold H A, Mockford B, Molloy D, McConway J, Ogonda L, Beverland D. "The transverse acetabular ligament: an aid to orientation of the acetabular component during primary total hip replacement: a preliminary study of 1000 cases investigating postoperative stability." J Bone Joint Surg Br. 2006; 88(7):883-6. With respect to the transverse acetabular ligament (TAL), cup orientation using the TAL and placement of a prosthetic implant in a total hip arthroplasty with respect to the acetabular labrum and the TAL can be as described therein.

Correct positioning of the acetabular cup can include the following aspects. Detection of the TAL and the acetabular rim can be used to orient the acetabular cup that is being overlayed or placed within the acetabulum. Augmented reality can be used to provide an optimized trajectory as well as the cup itself, which can be overlayed on the native anatomy to provide guidance for the surgeon. A color code can be used to provide feedback to the operator—e.g., red meaning the operator is outside a target safe zone, green meaning the operator can proceed with the specific orientation. With respect to the target zone, an operator can plan to place the implants anatomically, or in modified, but planned alignment. Various augmented reality views including where a tool is being used to prepare a surgical site for implantation of a prosthetic joint, including mixed reality red and green color codes of trajectories and arrow directions can be used to provide feedback to the operator.

The present technology can be used to guide depth of bone surface preparation by reaming or cutting operations. In certain embodiments, a QR code can be included on an acetabular reamer, which can be used to track bone removal/loss. Augmented reality guidance can therefore realize the goal of obtaining near complete coverage of the acetabular component. True floor of acetabulum (lamina interna) can be used as marker for depth of reaming. One or more images can be formed from operative imaging combined with a predetermined surgical plan that visually displays local progress to a desired bone topography for seating an implant. As noted, it is also possible to include and/or combine preoperative images (e.g., radiographic images, MRI, etc.) to extend the augmented reality display beyond what is visible within the surgeon's direct line of sight. Hip biomechanics (e.g., leg length, femoral offset, etc.) can be verified by visually overlapping the native hip with the hip replacement prosthetic that is visible in the surgical area.

Knee arthroplasty is another application of the present technology, which includes unicompartmental knee arthroplasty (UKA), patellofemoral joint replacement, bicompartmental knee arthroplasty and total knee arthroplasty. The knee is a hinge type joint formed by articulations between the femur, tibia, and patella. During TKA, all articulating surfaces are replaced (+/−patella). With UKA, only the medial or lateral aspect is replaced, where a defect is concentrated on one side of the joint. Various types of knee registration landmarks can be employed in the present technology. With respect to bone landmarks, these can include the medial and lateral femoral condyles, intercondylar notch, tibial spines, and tibial plateau, as well as other hard (e.g., bone) and soft tissue (e.g., ligament) landmarks.

Various types of augmented reality guidance can be used to optimize bone cuts in knee replacements. Using relevant anatomical markers, the present technology can detect a point of deepest erosion and can measure a proposed cut to be a predetermined distance (e.g., 2 mm) below this and at a predetermined anatomical posterior tibial slope (e.g., 7 degrees). The angle of the cut can be determined using preoperative radiographs indicating the depth of resection at various landmarks, e.g., medial edge of tibial plateau, mid-plateau, and adjacent to the intercondylar eminence. The tibial component can be overlayed on the tibia in the augmented reality presentation to the surgeon, where the tibial component can be shown in a desired position and an area of bone to be cut can be highlighted. Once the surgeon is satisfied with the position, or the position meets the desired operative parameters, it can be approved and with the use of QR codes on the saw/burr or guide, for example, the augmented reality display can monitor and update the progress of the cut. One or more optimal trajectories and/or desired surfaces can be color coded green and red for satisfactory initiation and progress versus indications of where an operation, including trajectory or surface is out of a desired zone or parameters. This can be done free hand or with a cutting jig using the augmented reality.

Various augmented reality representations can be used for showing a tibial implant being overlayed on the bone. Images can be augmented to represent a level of resection as well as orientation of a desired tibial bone cut. A distal femoral cut can also be referenced off of the tibial cut using a spacer block. This can ensure that the femur is parallel to the tibia, and allow standard cutting blocks to complete the bony preparation. Augmented reality depictions can show virtual tools, pathways, and tracks, including how a tool or instrument should be positioned used to prepare a knee joint for receipt of a prosthesis to obtain a desired geometry.

Certain embodiments of the present technology can further include various aspects relating to the augmented and/or mixed reality system. For example, the system can further include a computer having a processor and a memory. The memory can have non-transitory processor-executable instructions directing the augmented reality display to generate and display or depict the bone preparation parameters and/or tool guidance parameters within the surgeon's line of sight at the surgical site, including representations of the surgical sight not directly visible to the surgeon. These augmented reality representations can be based upon selection and/or identification of certain hard and/or soft tissue landmarks or reference points, which can be identified in the augmented reality image. In particular, processor-executable instructions can permit the computer to automatically identify and overlay augmented guidance based upon a surgical plan or modification of a surgical plan as directed by the surgeon or an operator. Certain embodiments can include one or more pre-programmed surgical plans, as well as artificial intelligence programming, which can be used to predict subsequent steps in a surgical plan, adjust steps in a surgical plan, and/or display options in the surgical plan using the augmented reality system. In this way, the present technology can provide established surgical plans and also can adapt to operations performed by the surgeon.

The augmented and/or mixed reality display can be configured to depict surgical guidance as part of a virtual window and/or as part of a virtual projection on the surgical site as viewed by the surgeon. In a more specific example, the augmented reality display can include a headset display wearable by the user or surgeon, the display being in communication with the computer. In an even more specific example, the computer can be integrated into the headset display wearable by the user. Certain embodiments include where the headset display can be a Microsoft HoloLens® having a tracking system (e.g., inertial measurement unit), integrated CPU and holographic processing unit, camera, and holographic projection lenses, for example, as described in U.S. Patent Application Publication No. 2018/0303563 to West et al., the entire disclosure of which including definitions is hereby incorporated herein by reference. One skilled in the art can select other suitable displays within the scope of the present disclosure.

The augmented and/or mixed reality surgical guidance that is generated by the computer and depicted on the surgical site can be further defined as a virtual display of one or more steps of a particular arthroplasty. In operation, various landmarks and/or markers, including QR codes on surgical tools, can be linked in the system so that position of one or more virtual projections can guide and ascertain one or more desired positions of surgical tools and/or prosthetic components. For example, the surgical tools can be provided with optical tracking means. Alternatively, augmented and/or mixed reality guidance can be placed in a virtually locked position with respect to the surgical site.

The present technology provides certain benefits and advantages over other augmented reality and mixed reality modalities associated with various types of arthroplasty. For example, certain augmented reality systems only use head mounted displays. The present technology, in contrast, can utilize projection mapping and contact lens augmented reality components, as well as other augmented/mixed reality viewing devices. Certain systems can be limited by having to perform re-registration, including multiple registration steps at various points in a surgical procedure. However, the present technology can forgo such re-registration events by using constant optimization based on feedback; e.g. by novel electromagnetic tracking, etc. In this way, the present technology can allow nudging of the registration throughout a step or procedure, where actual registration for augmented reality correlation only occurs once, providing a real time imaging modality. In addition, arthroplasty relates to open surgical procedures, so there is no need to re-register for motion or displacement of the patient using the present technology, as once the anatomy is registered, markers can be placed within the surgical site, not external, so that the augmented reality continuously knows if the anatomy has moved.

Other technologies may be limited by using only optical tracking, which is not ideal in an operating room because of the many individuals around the operating table and surrounding space that can block a line of sight. The present technology can overcome these limitations by incorporation of markerless tracking, including tracking technologies such as electromagnetic tracking that do not interfere with operating room equipment. For example, one of the major issues is what everyone around the operating tables sees. The present technology overcomes these limitations using a "shared view," where others using the augmented reality system can see what the primary operator sees. This can be important as the people around the operating table can all be standing in different directions and have different perspectives of the surgical site. The present technology therefore allows others to have the same view as the primary operator who is often the only one standing in the ideal location to view the surgical site. The augmented reality image can also be fixed to an ideal location, so when the primary operator turns his/her head, the image can remain fixed with the anatomy; e.g., mixed reality. As well, surgeries can take hours and the operators/surgeons tend to look around at other participants and equipment, other areas of the operating room, etc. and not solely at the surgical site. The mixed augmented reality of the present technology can therefore selectively turn off when the operator wants it to, or needs it to; e.g., by voice, command, by hand gesture or even by turning his/her head more than 45 degrees. In this way, when the surgeon looks to the side to get an instrument etc. from a nurse or surgical technician, the image can turn off if it is on the mode to do so. This can be personalized for the surgeon.

Many augmented reality systems depend on preoperative imaging for registration. Unlike such systems, the present technology can use intraoperative registration without any preoperative images. It is, however, possible to optionally incorporate preoperative/intraopertive images. In lieu of this preoperative imaging reliance, registration by the present technology can include the use of anatomical landmarks, like computer-assisted navigation, to create the augmented/mixed reality image. Intraoperative registration can include the identification of specific bone and soft tissue landmarks. This can either generate the image, or use artificial intelligence to create the image from an anatomy atlas; e.g., create a virtual joint by artificial intelligence from an atlas or database that most closely matches the patient's anatomy. Registration can be done for all the areas of the surgical site that are visible. For the areas not visible in the surgical site, the registration can be done by palpation or using other modalities, such as ultrasound. This can image and mark either the bone in question or the axis of alignment. Seeing the bone outside of the operative site allows the operator to prepare the bone without the risk of perforation or breaking it. For example, in the direct anterior approach of hip arthroplasty, the operator can broach the femur more safely by knowing its position, and canal size by the ultrasound, thereby seating the correct sized broach and implant in the correct alignment. In the knee, it can ensure that the implant is perpendicular to the long access of the tibia, etc. Ultrasound registration can also allow for a more minimally invasive incision and operation since the bone can be identified outside the surgical site to create a larger image. Ultrasound for registration can also identify a depth of bone and a width of the bone to ensure selection of an appropriate component; e.g., length of screw, canal filling implant, etc. What is more, ultrasound can be used as a soft tissue sensor to determine a balance of the soft tissues. In a knee, it can determine the flexion and extension gaps so as to indicate if further soft tissue releases are required, if the implant size should be changed, or its orientation modified. This can be done in conjunction with artificial intelligence.

Use of artificial intelligence in the present systems and methods can be in conjunction with display of augmented/mixed reality. Artificial intelligence can be voice or gesture activated. The artificial intelligence component can be used preoperatively or intraoperatively. Preoperatively, like in robotics, artificial intelligence can determine the size, location, and orientation of the implants. Preoperatively, artificial intelligence can recognize impingement, biomechanics, and kinematics of the planned surgeries. Artificial intelligence planning can then be used intraoperatively for the augmented/mixed reality to provide markers for the correct location and orientation of the implant components. Artificial intelligence can also indicate the depth of bone removal. Intraoperatively, the constant optimization of the registration can indicate if the implants are in a good position, or need to be modified. For example, if the implant positioning results in leg shortening or loss of offset, artificial intelligence can let the operator know and suggest a corrective maneuver—such as an increased head length. As well, after measuring knee soft tissue kinematics, by ultrasound, sensor or other means, the artificial intelligence can update the plan to adjust knee implant size and or position as needed. As such, the artificial intelligence can give feedback to recreate the kinematics and biomechanics of the joint.

An addition to the use of artificial intelligence is the ability to touch the control panel of a robot, computer-assisted navigation system, and/or analytic system with a virtual control panel. This functionality eliminates the need for the operator to divert their attention or move their body to do this on a sterile panel or have an assistant in the room performing the commands that the surgeon wants executed.

In certain embodiments, the present technology should be understood to provide methods of performing arthroplasty on a surgical site of a patient by an operator using an augmented reality system. These methods can include the provision of a system that can include an imaging device, a display device, and a computer system having a processor and a memory. The imaging device can be configured to acquire a first image of the surgical site and the display device can be configured to display an augmented reality depiction of the surgical site. The computer system can be in communication with the imaging device and the display device. The memory of the computer system can include tangible, non-transitory, machine-readable instructions.

The memory can include one or more types of memory and can include any type suitable to the local application environment. Examples include where the memory can include various implementations of volatile and/or nonvolatile data storage technology, such as a semiconductor-based memory device, a magnetic memory device and system, an optical memory device and system, fixed memory, and removable memory. For example, the memory can include one or more of random access memory (RAM), read only memory (ROM), static storage such as a magnetic or optical disk, hard disk drive (HDD), or any other type of non-transitory machine or computer readable media, as well as combinations of the aforementioned types of memory.

Instructions stored in the memory can include program instructions or computer program code that, when executed by the processor, enables the computer system to perform operations and tasks as described herein. Machine-readable instructions can be embodied by one or more various modules. Such modules can be implemented as one or more of functional logic, hardware logic, electronic circuitry, software modules, and the like. The processor of the computer system can be configured to execute the instructions or modules stored in the memory. In certain embodiments, the memory can include a registration module configured to correlate a predetermined surgical plan with the first image (acquired by the imaging device) to generate the augmented reality depiction (displayed by the display device) of the surgical site using the first image.

In employing such systems, the present methods can include the following actions. The operator can view the augmented reality depiction of the surgical site using the display device. Accordingly, the operator can prepare a portion of the surgical site using a surgical instrument guided by the augmented reality depiction to form a prepared site. The operator can then position a prosthetic implant at the prepared site to form a positioned implant.

The imaging device can be configured to acquire and update the first image of the surgical site in real time. That is, the first image can include a series of images updated at a particular frequency, where the first image can include a video stream having a refresh rate substantially imperceptible to the human eye. In this way, the registration module of the computer system can correlate the predetermined surgical plan with an updated, or continuously updated, first image to generate the augmented reality depiction of the surgical site using the first image.

Various types of imaging devices can be employed. Examples include various numbers of optical cameras, stereoscopic cameras configured to collect three dimensional data, cameras able to acquire images of various portions of the electromagnetic spectrum, and other imaging devices using other imaging modalities, including one or more devices capable of acquiring a radiographic image, an ultrasound image, a magnetic resonance image, and/or a computerized tomography image. In certain embodiments, the first image can include a composite, average, or modification of an image using one or more additional images.

It is further possible that the operator can move a portion of the surgical site of the patient, and when this happens, the imaging device can acquire and update the first image of the moved portion of the surgical site in real time. For example, the operator may move the portion of the surgical site and/or the patient themselves, either directly with their hands and/or using a surgical instrument, or indirectly by controlling an articulating surface on which the patient is lying and/or coupled thereto. The operator also may direct another individual to move the patient in some manner. The patient and the surgical site can be moved as necessary to change access to the surgical site during the predetermined surgical plan.

Various types of display devices can be employed. Examples include one or more of a head mounted display, a screen, a window, and a projection. Different display devices can be used at different portions of executing the predetermined surgical plan. It is also possible to have the display device include multiple displays, where different displays can further show different embodiments of the augmented reality depiction. For example, one display can show an augmented reality depiction based upon real time while another display can show an augmented reality depiction of an end point of a particular step or operation of the predetermined surgical plan. Instructions, including text, symbols, indicia, and animations, as well as guidance, and/or historical data can be part of an augmented reality depiction shown on a display.

The memory of the computer system can include an image module, where the image module can include a preexisting image of the surgical site. Examples of a preexisting image include one or more images acquired earlier in time to the first image acquired by the imaging device. Further examples of a preexisting image include images acquired from various imaging devices, such as an optical image of visible light taken by a digital camera, a radiographic image, an ultrasound image, a magnetic resonance image, and/or a computerized tomography image. In this way, the registration module can be configured to correlate the predetermined surgical plan with the first image and the preexisting image to generate the augmented reality depiction of the surgical site using the first image. For example, this allows the augmented reality depiction to include a real time image of the surgical site incorporating or overlaid with an augmented reality depiction of portions of the surgical site (e.g., bone) taken from a radiographic image. As such, the first image can include a portion of the surgical site viewable by the operator and the preexisting image can include a portion of the surgical site not viewable by the operator; e.g., a portion of bone not exposed at the surgical site.

The memory of the computer system can include a predictive module, where the predictive module can be configured to correlate a predictive image based upon the predetermined surgical plan with the first image to generate the augmented reality depiction of the surgical site using the first image. In this way, the predictive module can match one or more anatomical landmarks from the first image with the predetermined surgical plan to position the predictive image in correlating the predictive image and the first image to generate the augmented reality depiction of the surgical site using the first image. One or more landmarks from an acetabulum, for example, can be identified in the first image and used to place or orient the predictive image based upon installation of an acetabular cup, where the augmented reality depiction can show how the acetabulum is to be modeled/modified by the surgical instrument for installation of the acetabular cup. The predictive module can include artificial intelligence, as well as image matching methods, which can be configured to ascertain known and/or expected landmarks within the surgical site based upon the predetermined surgical plan.

Where the imaging device is configured to acquire and update the first image of the surgical site in real time, the operator, in preparing the portion of the surgical site using the surgical instrument guided by the augmented reality depiction to form the prepared site, can reveal one or more additional anatomical landmarks at the surgical site. The predictive module can then match one or more additional anatomical landmarks from the first image with the predetermined surgical plan to position or reposition the predictive image in correlating the predictive image and the first image to generate the augmented reality depiction of the surgical site using the first image. This aspect of the predictive module can allow the augmented reality depiction to be updated and improved during the arthroplasty procedure. For example, as more bone is exposed by the operator during the arthroplasty, the predictive module can use the successive accumulation of landmarks in the first image (as continuously being acquired) to provide placement of the predictive image (e.g., an acetabulum model) in the augmented reality depiction with increasing accuracy and confidence.

In certain embodiments, where the imaging device is configured to acquire and update the first image of the surgical site in real time, the memory of the computer system can include a positioning module. The positioning module can be configured to correlate the positioned implant at the prepared site with the predetermined surgical plan and determine an implant deviation. For example, the predetermined surgical plan may include certain geometric parameters (e.g., distances, angles, curvatures, etc.) and the positioning module can ascertain whether and how the prosthetic implant positioned at the prepared site by the operator deviates from geometric parameters in the predetermined surgical plan. In this way, the operator can adjust the positioned implant to account for the implant deviation to form a repositioned implant. The augmented reality depiction can therefore guide the operator to easily reposition the prosthetic implant using a virtually depicted optimized position.

In certain embodiments, again where the imaging device is configured to acquire and update the first image of the surgical site in real time, the memory of the computer system can include a tracking module. The tracking module can be configured to determine a track of the surgical instrument using the first image. In this way, the registration module can be further configured to generate the augmented reality depiction of the surgical site by including a predetermined approach of the surgical instrument to the surgical site based upon the track of the surgical instrument determined using the first image by the tracking module. The augmented reality depiction can therefore inform the operator of a preferred track representing the predetermined approach according to the predetermined surgical plan, whether the instrument comports with the preferred track in real time, and/or if and/or how the instrument deviates from the preferred track. In particular, the augmented reality depiction can identify whether the track of the surgical instrument matches the predetermined approach. This allows the operator to proceed with operation of the surgical instrument in accordance with the predetermined surgical plan, including preparation of the surgical site to form the prepared site as well as positioning of the prosthetic implant at the prepared site to form the positioned implant.

The memory of the computer system can include a modification module configured to modify the predetermined surgical plan. In this way, the display device can be further configured to display an augmented reality depiction including a control panel configured to respond to a gesture of the operator to communicate with the modification module and allow the operator to modify the predetermined surgical plan. The computer system can also be in communication with a remote system, where the remote system can be configured to access the modification module, thereby allowing a remote operator to modify the predetermined surgical plan. These embodiments can include various aspects of telemedicine and include where the remote operator can facilitate or guide the arthroplasty and/or adapt the predetermined surgical plan based upon progress of the operator in preparing the portion of the surgical site and/or progress of the operator in positioning the prosthetic implant.

The present technology can be adapted to various aspects of several types of arthroplastic procedures. The operator can accordingly remove, resurface, shape, augment (e.g., apply bone cement) various portions of a musculoskeletal joint in preparing the portion of the surgical site using the surgical instrument guided by the augmented reality depiction to form the prepared site. The present technology is particularly adapted to hip replacement and knee replacement procedures; however, these particular procedures and related examples and figures provided herein should be understood as not limiting to application of the present technology to other procedures relating to other musculoskeletal joints, including joints such as the ankle, elbow, and shoulder.

In certain embodiments, the present technology should be understood to provide augmented reality systems for performing arthroplasty on a surgical site of a patient by an operator. Such systems can include an imaging device, a display device, and a computer system. The imaging device can include imaging devices as described herein, where the imaging device can be configured to acquire and update a first image of the surgical site in real time. The display device can include display devices as described herein, where the display device can be configured to display an augmented reality depiction of the surgical site. The computer system can include computer systems as described herein, where the computer system can have a processor and a memory, and the computer system can be in communication with the imaging device and the display device. The memory of the computer device can include one or more of a registration module, an image module, a predictive module, a positioning module, a tracking module, and a modification module.

The modules can include the aspects described herein, including the following features. The registration module can be configured to correlate a predetermined surgical plan with the first image to generate the augmented reality depiction of the surgical site using the first image. The image module can include a preexisting image of the surgical site, where the registration module can be configured to correlate the predetermined surgical plan with the first image and the preexisting image to generate the augmented reality depiction of the surgical site using the first image. The predictive module can be configured to correlate a predictive image based upon the predetermined surgical plan with the first image to generate the augmented reality depiction of the surgical site using the first image. The positioning module can be configured to correlate the positioned implant at the prepared site with the predetermined surgical plan and determine an implant deviation. The tracking module can be configured to determine a track of the surgical instrument using the first image, where the registration module can be further configured to generate the augmented reality depiction of the surgical site including a predetermined approach of the surgical instrument to the surgical site based upon the track of the surgical instrument determined using the first image by the tracking module. The modification module can be configured to modify the predetermined surgical plan, where the display device can be further configured to display an augmented reality depiction including a control panel configured to respond to a gesture of the operator to communicate with the modification module and allow the operator to modify the predetermined surgical plan. The computer system can be in communication with a remote system, where the remote system can be configured to access the modification module, thereby allowing a remote operator to modify the predetermined surgical plan.

In certain embodiments, the present systems can further include the following aspects. The first image can include a portion of the surgical site viewable by the operator and the preexisting image can include a portion of the surgical site not viewable by the operator. The predictive module can match one or more anatomical landmarks from the first image with the predetermined surgical plan to position the predictive image in correlating the predictive image and the first image to generate the augmented reality depiction of the surgical site using the first image. The predictive module can match the one or more additional anatomical landmarks from the first image with the predetermined surgical plan to position or reposition the predictive image in correlating the predictive image and the first image to generate the augmented reality depiction of the surgical site using the first image.

EXAMPLES

Example embodiments of the present technology are provided with reference to the several figures enclosed herewith.

Figure 2:
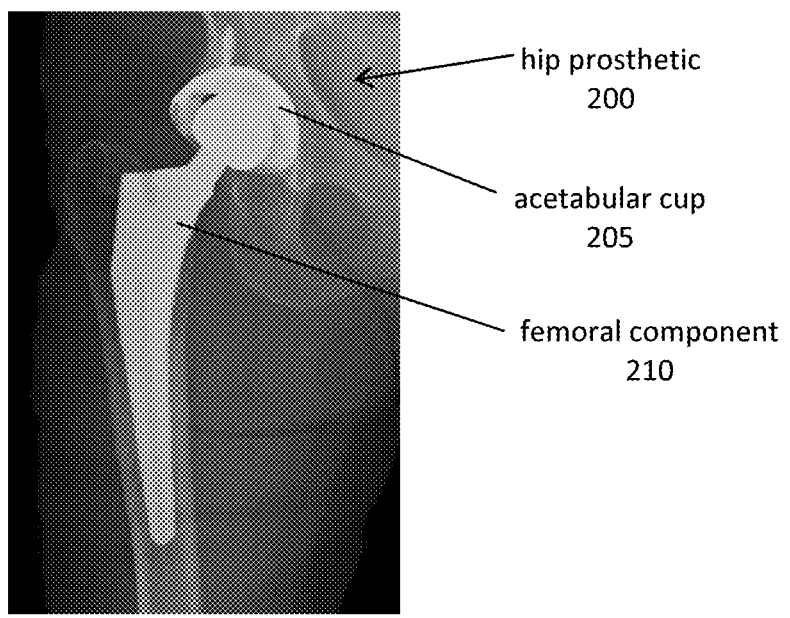
FIG. 2 shows a radiographic image of a total hip arthroplasty, depicting an acetabular cup and a femoral component of a prosthetic implant.

Methods and systems of the present technology can be used to perform arthroplasty on a surgical site of a patient by an operator using an augmented reality system. A particular embodiment of arthroplasty includes a hip replacement. With reference to FIG. 1, a schematic view of a hip joint 100, depicting an acetabulum 105 of a pelvis and a femoral head 110 of a femur 115 is shown. With reference to FIG. 2, a radiographic image of a total hip arthroplasty is shown, depicting a hip prosthetic 200 including an acetabular cup 205 and a femoral component 210.

Figures 3A, 3B:
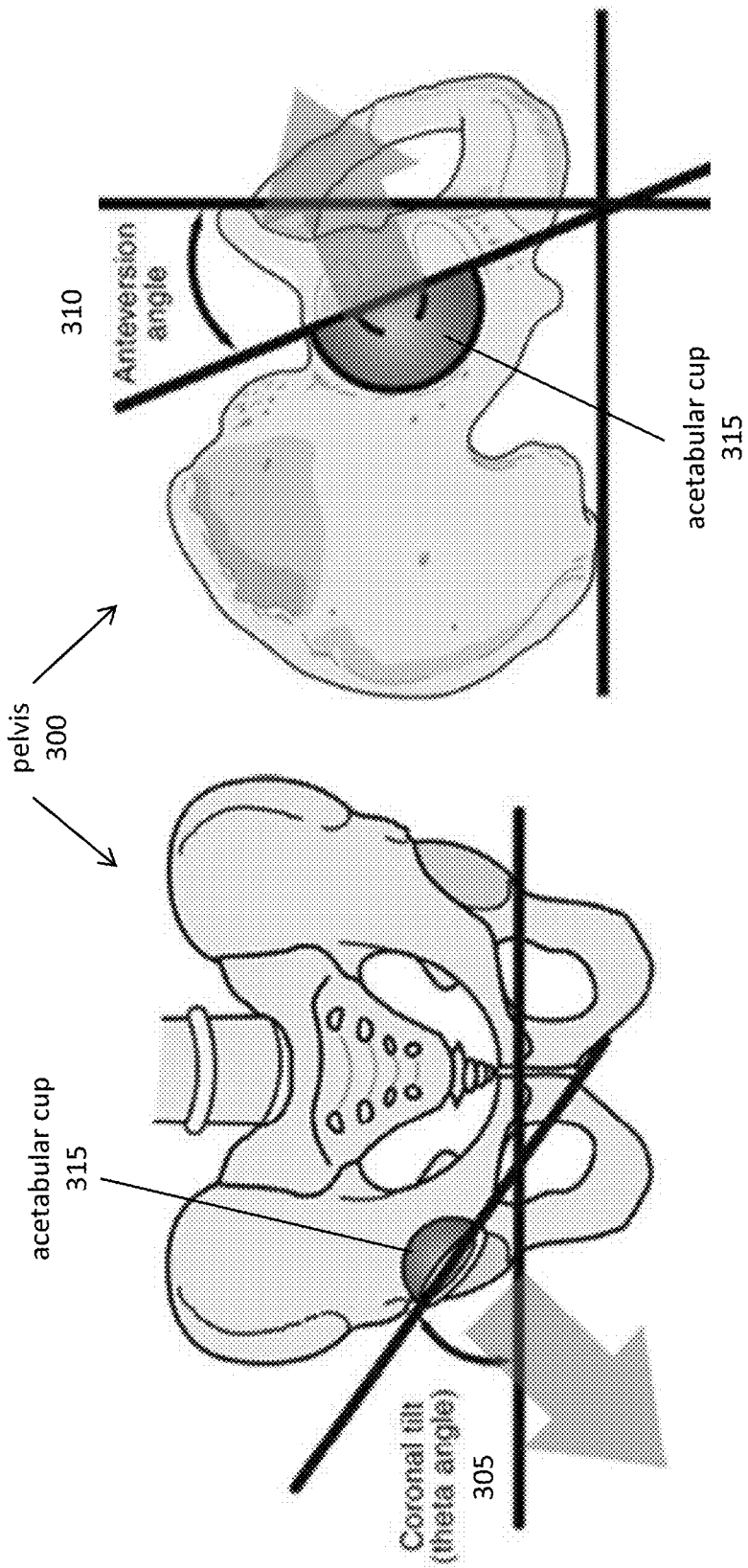
FIGS. 3A and 3B show schematic views of a coronal tilt (theta angle) and an anteversion angle, respectively, with respect to placement of an acetabular cup in an acetabulum of a pelvis.

With reference to FIGS. 3A and 3B, a coronal tilt (theta angle) 305 and an anteversion angle 310, respectively, can be optimized with respect to placement of an acetabular cup 315 in following preparation of an acetabulum of a pelvis 300 using a surgical instrument.

Figure 4B:
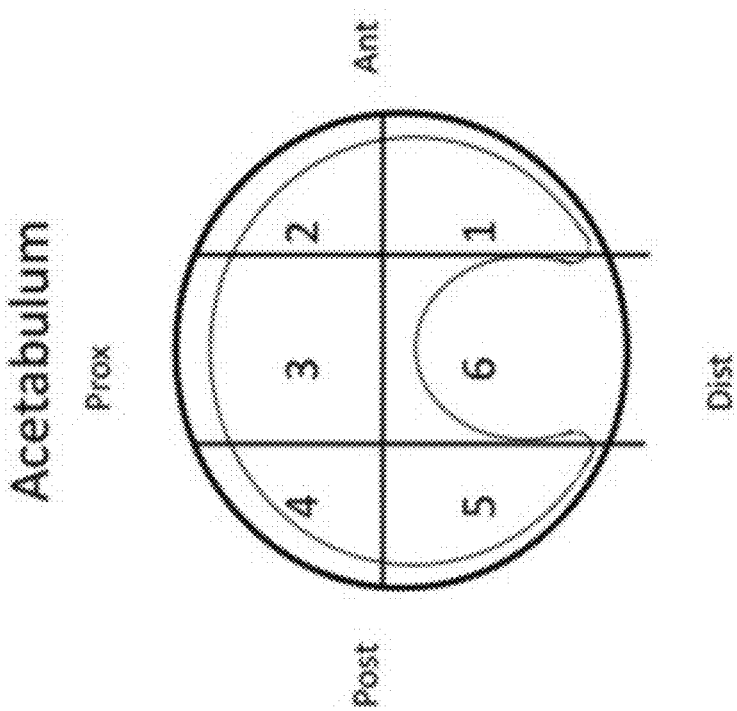
FIGS. 4A and 4B show schematic views of a computer mapping image of an acetabulum of a pelvis and a schematic of mapping regions for the acetabulum, respectively.
Figure 4A:
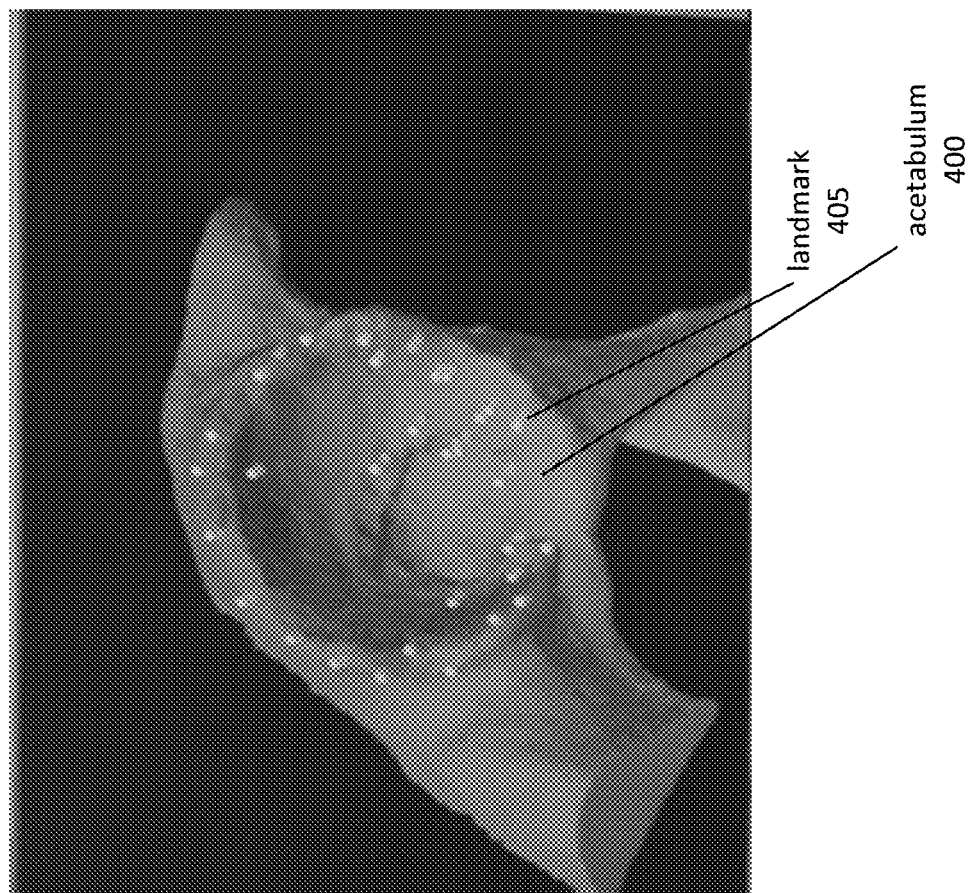
Figure 5B:
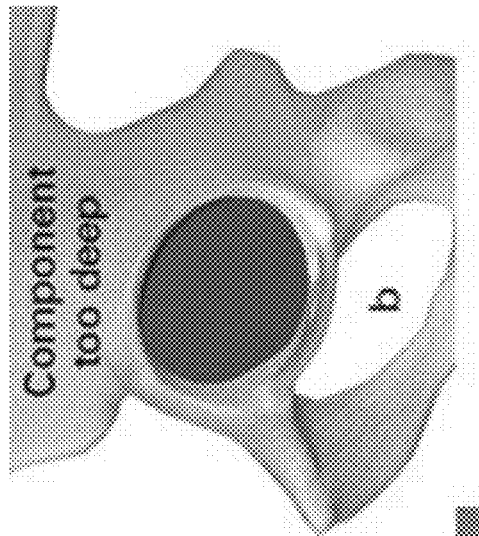
FIGS. 5A-5E show schematic views of placement variations in reference to a desired or correct placement of an acetabular cup in an acetabulum of a pelvis.
Figure 5E:
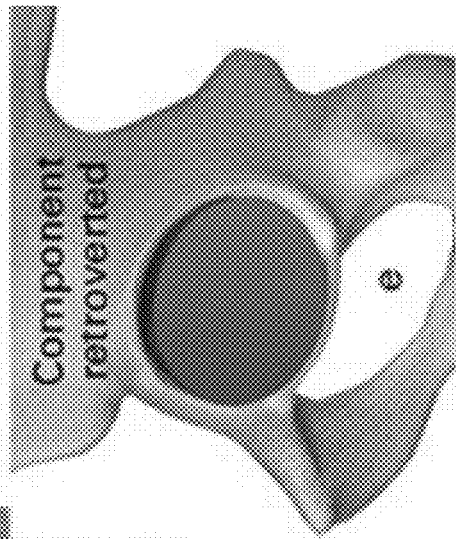
Figure 5C:
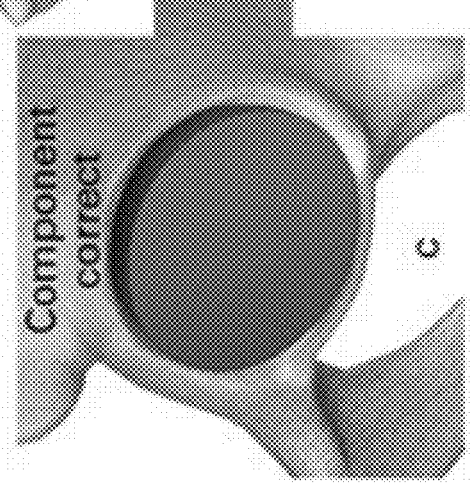
Figure 5A:
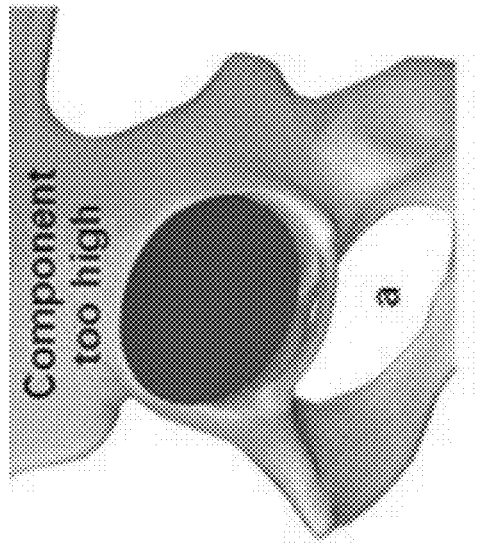
Figure 5D:
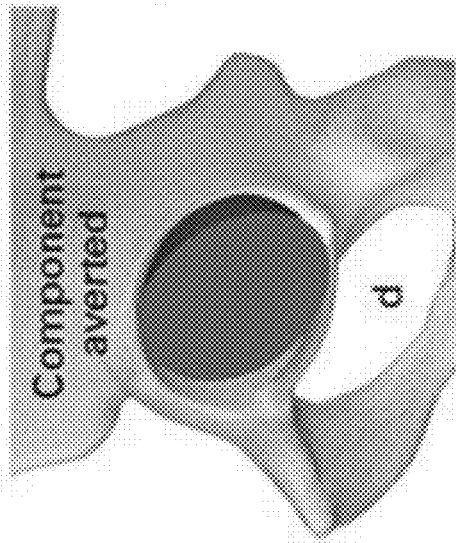

With reference to FIG. 4A, a computer mapping image of an acetabulum 400 and landmarks 405 related thereto are shown. The landmarks 405 can be used in generating the augmented reality depiction of the surgical site and in correlating a predictive image based upon the predetermined surgical plan with the first image to generate the augmented reality depiction of the surgical site. FIG. 4B provides a schematic of mapping regions (1-6) for the acetabulum in reference to anterior (Ant), posterior (Post), proximal (Prox), and distal (Dist) regions thereof, where landmarks can be categorized based upon these mapping regions and where landmarks can be ascertained by a predictive module as they appear during preparation of the surgical site.

With reference to FIGS. 5A-5E, schematic views are shown of placement variations in reference to a predetermined position (e.g., a desired or correct placement) of an acetabular cup in an acetabulum of a pelvis. For example, a positioning module can correlate the positioned acetabular cup at the prepared site with the predetermined surgical plan and determine an implant deviation, if present, and can further determine if/when the implant is in the predetermined position. The augmented reality depiction can virtually display the predetermined position to the operator. In this way, the operator can adjust the positioned implant from the deviated position to account for the implant deviation to form a repositioned implant in the predetermined position.

Figure 6:
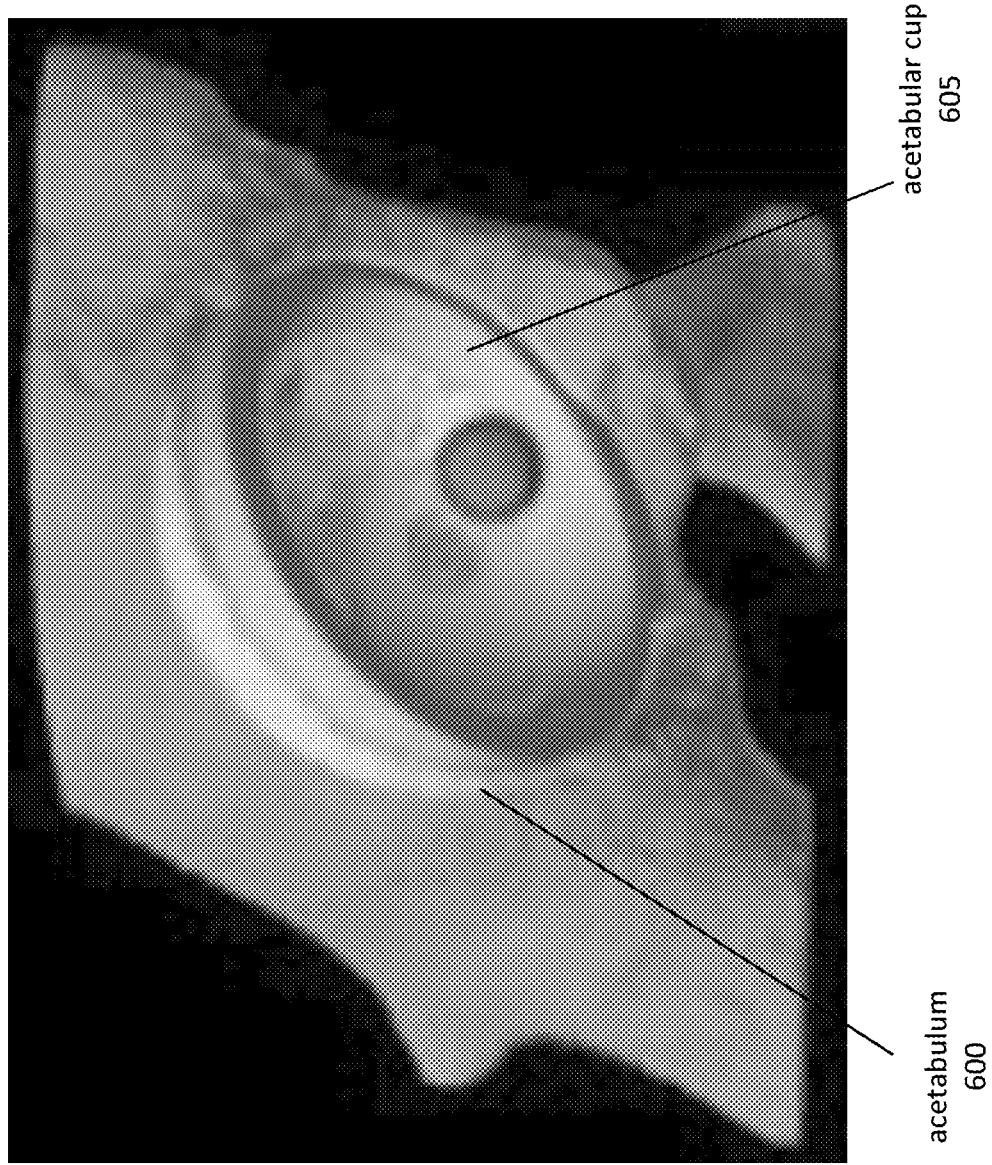
FIG. 6 shows a schematic of a computer mapping image of an acetabular cup being implanted into an acetabulum of a pelvis.

With reference to FIG. 6, a schematic of a computer mapping image of an acetabular cup 605 being implanted into an acetabulum 600 is shown. The computer mapping image can be provided as part of the augmented reality depiction to the operator.

Figure 7:
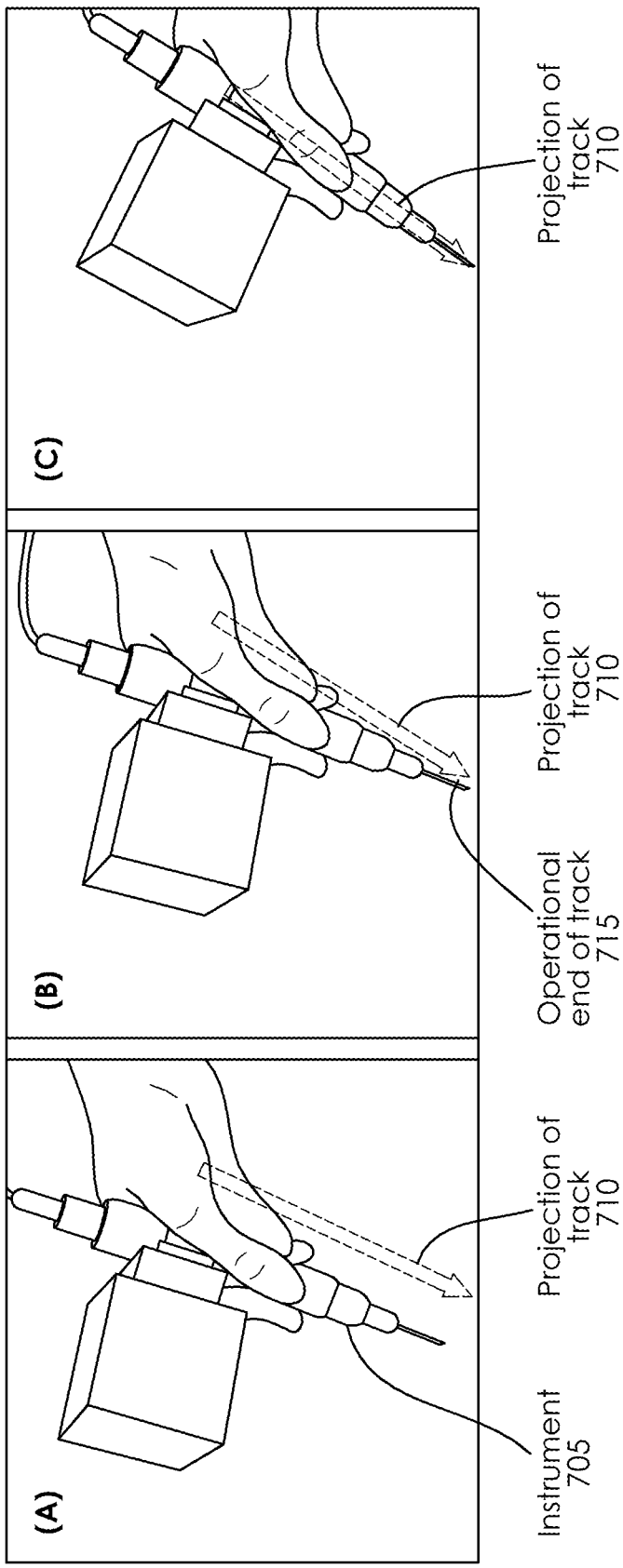
FIGS. 7A-7C show a series of augmented reality views of using a tool to prepare a surgical site for implantation of a prosthetic joint.

With reference to FIGS. 7A-7C, show a series of augmented reality views of an operator using a surgical instrument 705 to prepare a surgical site for implantation of a prosthetic joint. FIG. 7A depicts the instrument 705 in relation to an augmented reality depiction of a projection of a track 710 for the instrument 705 based upon a predetermined surgical plan. As can be seen in FIG. 7A, the instrument 705 position does not match the track 710. FIG. 7B depicts the operational end of the instrument 705 relocated to an operational end 715 of the track 710. FIG. 7C depicts the operational end of the instrument 705 relocated to the operational end 715 of the track 710 and the remainder of the instrument 705 positioned in line with the angle set by the track 710. In this way, the augmented reality depiction can guide the operator with the optimal location and approach in preparing the surgical site using the instrument 705.

Figure 8:
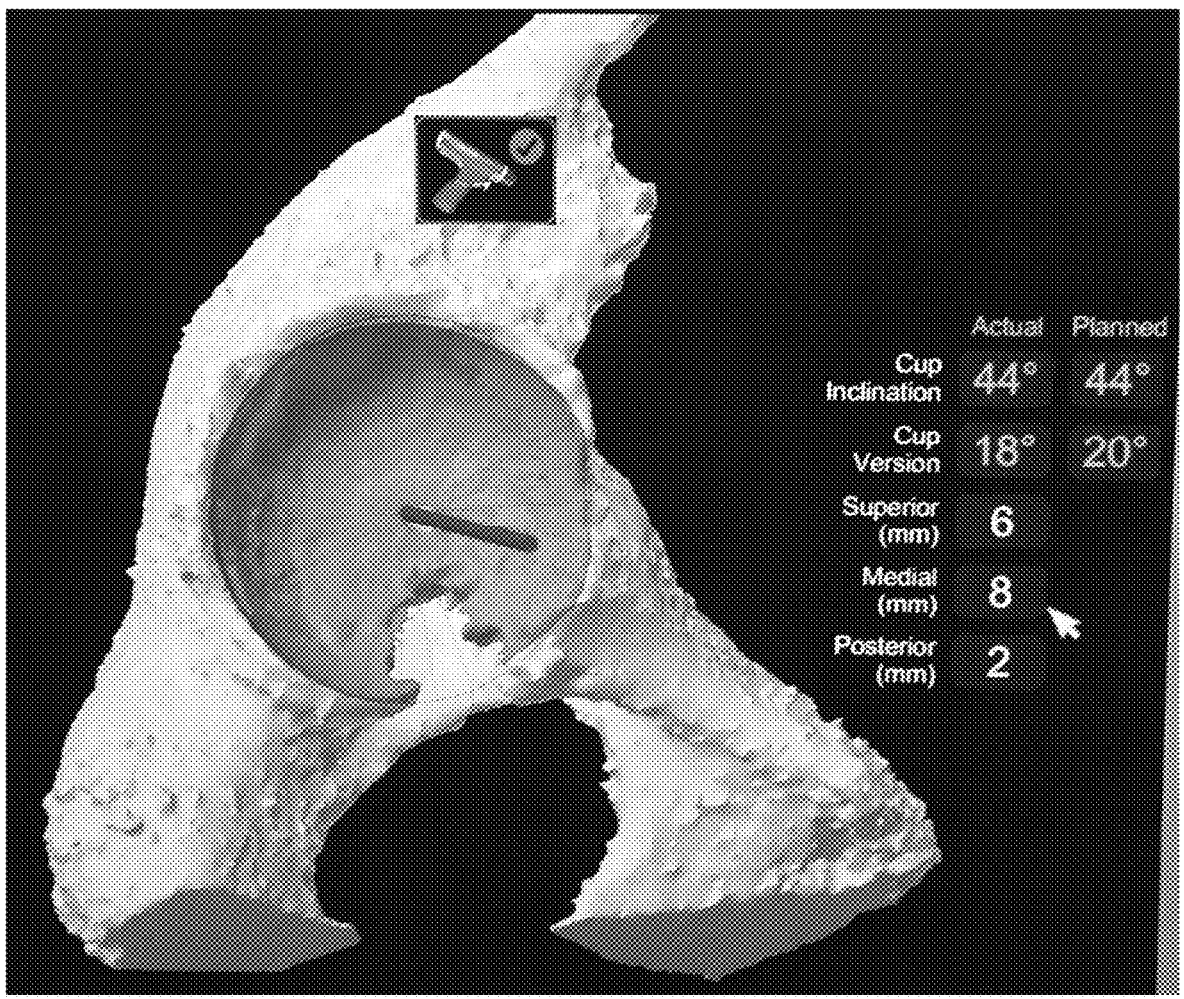
FIG. 8 shows a schematic of a computer mapping image of preparing an acetabulum of a pelvis for receipt of an acetabular cup to obtain a desired geometry.

With reference to FIG. 8, a schematic of a computer mapping image of preparing an acetabulum of a pelvis for receipt of an acetabular cup to obtain a desired geometry is shown. The augmented reality depiction of the surgical site can show the operator where and how to prepare the bone surface for receiving the implant. Likewise, the positioning module can be used to correlate the positioned implant at the prepared site with the predetermined surgical plan and determine an implant deviation, where the operator can adjust the positioned implant to account for the implant deviation to form a repositioned implant in accordance with the predetermined surgical plan, for example.

Figure 9:
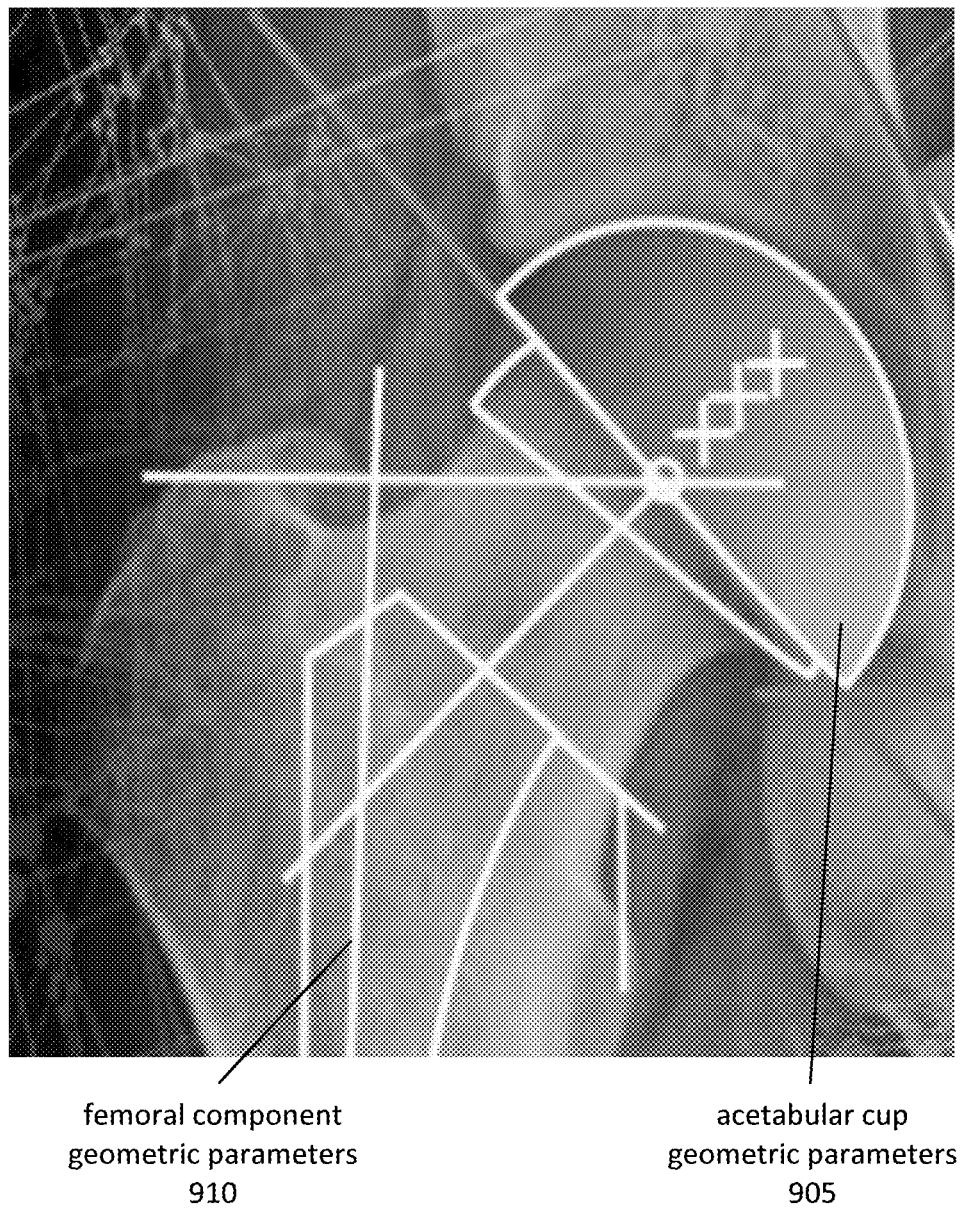
FIG. 9 shows an annotated radiographic image of a hip joint including considerations of leg length and offset, as shown.

With reference to FIG. 9, an annotated radiographic image of a hip joint is shown that includes an augmented reality depiction of certain geometric parameters for preparing the surgical site and positioning a prosthetic implant at the surgical site to produce an optimized prosthetic joint. In particular, example femoral component geometric parameters 910 are shown in relation to acetabular cup geometric parameters 905, where the relative angles, spacings, and curvatures provide optimal interactions between the cooperating prosthetic components. Examples include leg length including the center of femoral head in relation to the tip of the greater trochanter or to the top of the lesser trochanter, and offset of the center of the femoral head in relation to the center of the femoral canal; e.g., piriformis fossa.

With reference to FIGS. 10A-10C, show schematic views of a total knee arthroplasty (TKA), a unicompartmental knee arthroplasty (UKA), and a radiographic image of a UKA, respectively, with various prosthetic knee components 1005.

Figures 11A, 11B:
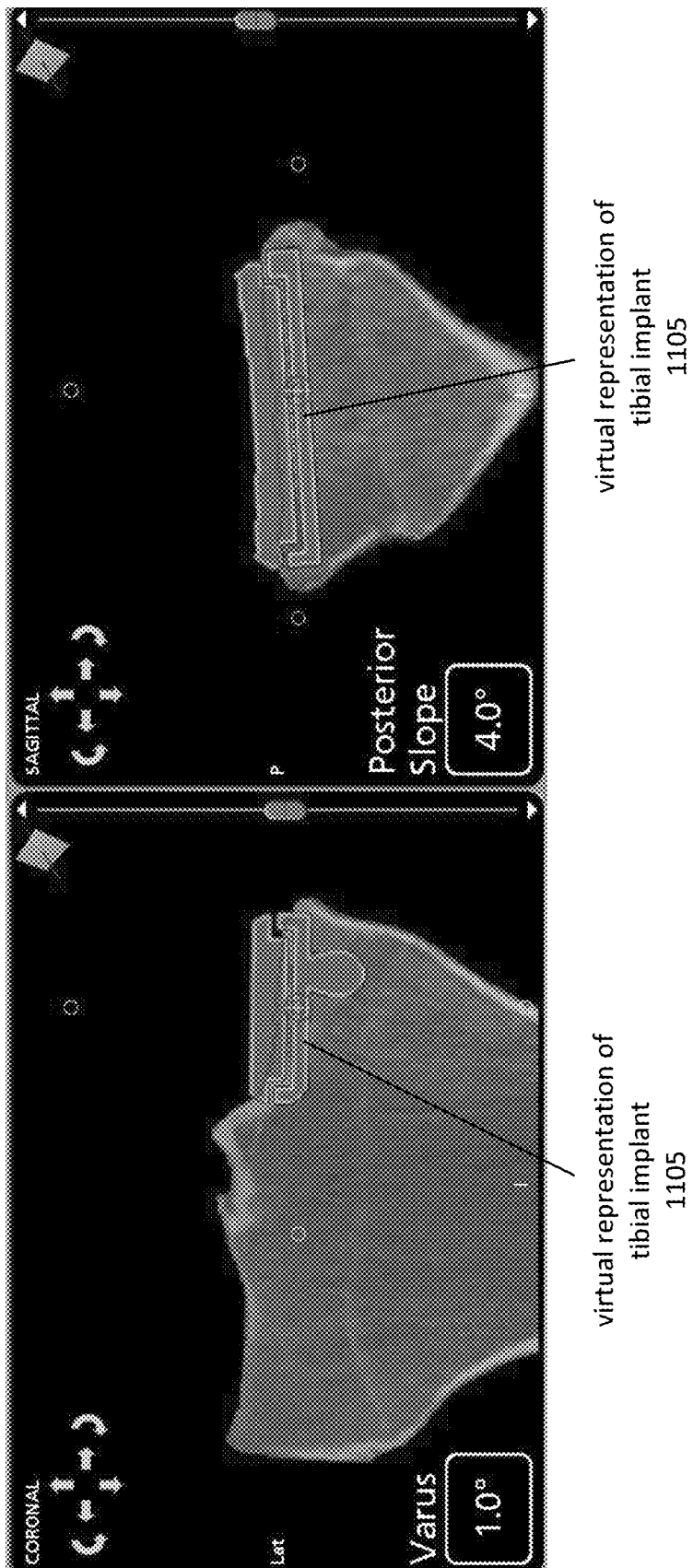
FIGS. 11A and 11B show schematics of computer mapping images for preparing portions of a knee joint for receipt of a prosthesis to obtain a desired geometry.

With reference to FIGS. 11A and 11B, show schematics of computer mapping images that can be provided as part of the augmented reality depiction of the surgical site in preparing portions of a knee joint for receipt of a prosthesis to obtain a desired geometry. In particular, virtual representations of a tibial implant 1105 are shown with respect to coronal and sagittal planes.

Figure 12:
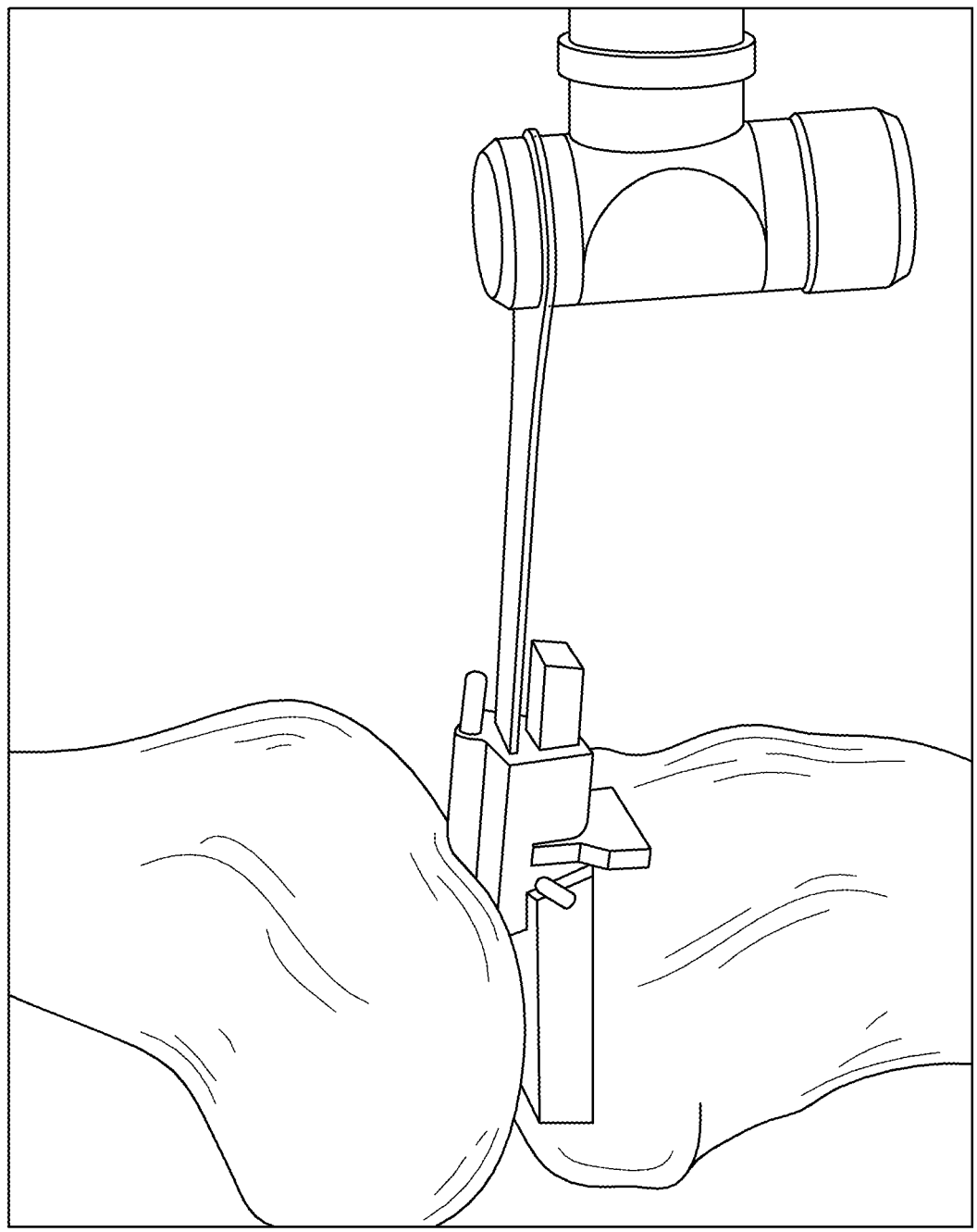
FIG. 12 shows a schematic of a tool used to prepare a knee joint for receipt of a prosthesis to obtain a desired geometry.

With reference to FIG. 12, a schematic of positioning a tool to prepare a knee joint for receipt of a prosthesis to obtain a desired geometry is shown. The tool position can be provided as part of the augmented reality depiction.

Figure 13:
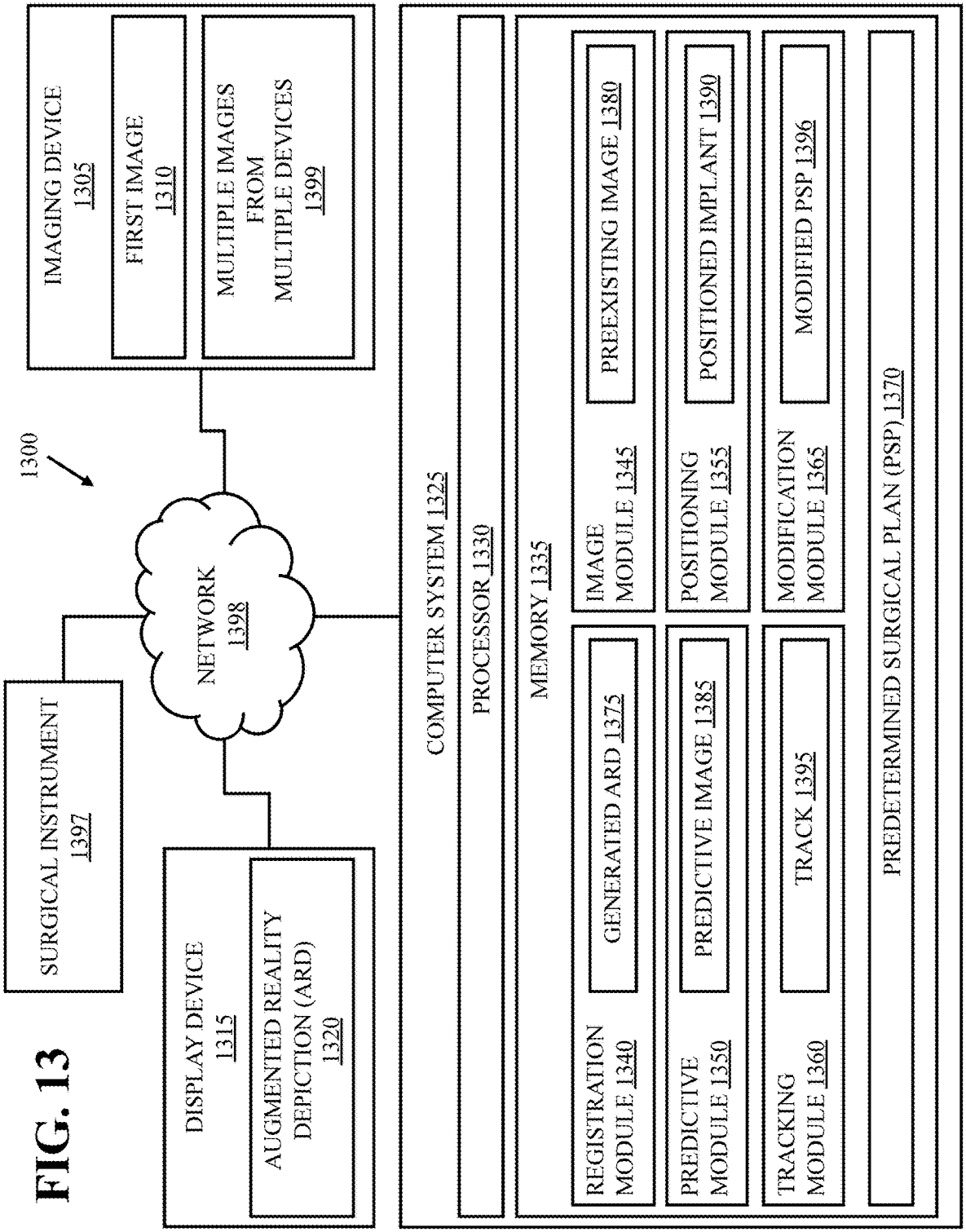
FIG. 13 shows a schematic view of an augmented reality system for performing arthroplasty on a surgical site of a patient by an operator.

With reference to FIG. 13, a schematic view of an augmented reality system 1300 for performing arthroplasty on a surgical site of a patient by an operator is shown. The augmented reality system 1300 can include an imaging device 1305, a display device 1315, and a computer system 1325 having a processor 1330 and a memory 1335. The imaging device 1305 can be configured to acquire and update a first image 1310 of the surgical site in real time. The display device 1315 can be configured to display an augmented reality depiction 1320 of the surgical site. The computer system 1325 can be in communication with the imaging device 1305 and the display device 1315, where communication can be via a network 1398 that can include wired and/or wireless communication. The memory 1335 can include one or more of a registration module 1340, an image module 1345, a predictive module 1350, a positioning module 1355, a tracking module 1360, and a modification module 1365. The memory 1335 can further include other modules and functionalities, including other tangible, non-transitory, machine-readable instructions to perform operations as described herein. The registration module 1340 can be configured to correlate a predetermined surgical plan 1370 with the first image 1310 to generate the augmented reality depiction 1320 of the surgical site using the first image 1310, as shown at 1375. The image module 1345 can include a preexisting image 1380 of the surgical site, where the registration module 1340 is configured to correlate the predetermined surgical plan 1370 with the first image 1310 and the preexisting image 1380 to generate the augmented reality depiction 1320 of the surgical site using the first image 1310. The predictive module 1350 can be configured to correlate a predictive image 1385 based upon the predetermined surgical plan 1370 with the first image 1310 to generate the augmented reality depiction 1320 of the surgical site using the first image 1310. The positioning module 1355 can be configured to correlate the positioned implant at the prepared site with the predetermined surgical plan 1370 and determine an implant deviation. The tracking module 1360 can be configured to determine a track 1395 of a surgical instrument 1397 using the first image 1310, where the registration module 1340 can be further configured to generate the augmented reality depiction 1320 of the surgical site including a predetermined approach of the surgical instrument 1397 to the surgical site based upon the track of the surgical instrument determined using the first image 1305 by the tracking module 1360. The modification module 1365 can be configured to modify the predetermined surgical plan 1370, where the display device 1315 can be further configured to display an augmented reality depiction 1320 including a control panel configured to respond to a gesture of the operator to communicate with the modification module 1365 and allow the operator to modify the predetermined surgical plan 1370 to form a modified predetermined surgical plan 1396. The computer system 1325 can be in communication with a remote system (not shown), where the remote system can be configured to access the modification module 1365, thereby allowing a remote operator to modify the predetermined surgical plan 1370 to form a modified predetermined surgical plan 1396.

The augmented reality system 1300 can include certain additional aspects. The imaging device 1305 can acquire multiple images and/or can include multiple imaging devices, including multiple imaging devices having multiple imaging modalities. In this way, the imaging device 1305 can acquire multiple images from multiple devices as shown at 1399. The first image 1305 can include a portion of the surgical site viewable by the operator and the preexisting image 1380 of the image module 1345 can include a portion of the surgical site not viewable by the operator. The predictive module 1350 can match one or more anatomical landmarks from the first image 1310 with the predetermined surgical plan 1370 to position the predictive image 1385 in correlating the predictive image 1385 and the first image 1305 to generate the augmented reality depiction 1320 of the surgical site using the first image 1310. The predictive module 1350 can also match one or more additional anatomical landmarks from the first image 1310 with the predetermined surgical plan 1370 to position or reposition the predictive image 1385 in correlating the predictive image 1385 and the first image 1310 to generate the augmented reality depiction 1320 of the surgical site using the first image 1310.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms, and that neither should be construed to limit the scope of the disclosure. In some example embodiments, well-known processes, well-known device structures, and well-known technologies are not described in detail. Equivalent changes, modifications and variations of some embodiments, materials, compositions and methods can be made within the scope of the present technology, with substantially similar results.

What is claimed is:

1. A method of performing arthroplasty on a surgical site of a patient by an operator using an augmented reality system, the method comprising:

providing a system including:
an imaging device including a camera and configured to acquire a first image of the surgical site including an anatomical landmark;
a display device configured to display an augmented reality depiction of the surgical site;
a computer system having a processor and a memory, the computer system in communication with the imaging device and the display device, the memory including:

a registration module configured to correlate a predetermined surgical plan with the first image including identifying the anatomical landmark to generate the augmented reality depiction of the surgical site using the first image;

viewing, by the operator, the augmented reality depiction of the surgical site using the display device;

preparing, by the operator, a portion of the surgical site using a surgical instrument guided by the augmented reality depiction to form a prepared site; and positioning, by the operator, a prosthetic implant at the prepared site to form a positioned implant.

2. The method of claim 1, wherein the imaging device is configured to acquire and update the first image of the surgical site in real time.

3. The method of claim 2, further comprising:
moving, by the operator, a portion of the surgical site of the patient;
wherein, the imaging device acquires and updates the first image of the moved portion of the surgical site in real time.

4. The method of claim 1, wherein the display device includes a member selected from a group consisting of a head mounted display, a screen, a window, a projection, and combinations thereof.

5. The method of claim 1, wherein the memory of the computer system includes an image module, the image module including a preexisting image of the surgical site, and the registration module is configured to correlate the predetermined surgical plan with the first image and the preexisting image to generate the augmented reality depiction of the surgical site using the first image.

6. The method of claim 5, wherein the first image includes a portion of the surgical site viewable by the operator and the preexisting image includes a portion of the surgical site not viewable by the operator.

7. The method of claim 1, wherein the memory of the computer system includes a predictive module, the predictive module configured to correlate a predictive image based upon the predetermined surgical plan with the first image to generate the augmented reality depiction of the surgical site using the first image.

8. The method of claim 7, wherein the predictive module matches one or more anatomical landmarks from the first image with the predetermined surgical plan to position the predictive image in correlating the predictive image and the first image to generate the augmented reality depiction of the surgical site using the first image.

9. The method of claim 8, wherein:
the imaging device is configured to acquire and update the first image of the surgical site in real time;
preparing, by the operator, the portion of the surgical site using the surgical instrument guided by the augmented reality depiction to form the prepared site includes revealing one or more additional anatomical landmarks at the surgical site; and
the predictive module matches the one or more additional anatomical landmarks from the first image with the predetermined surgical plan to position or reposition the predictive image in correlating the predictive image and the first image to generate the augmented reality depiction of the surgical site using the first image.

10. The method of claim 1, wherein:
the imaging device is configured to acquire and update the first image of the surgical site in real time;
the memory of the computer system includes a positioning module, the positioning module configured to correlate the positioned implant at the prepared site with the predetermined surgical plan and determine an implant deviation; and
adjusting, by the operator, the positioned implant to account for the implant deviation to form a repositioned implant.

11. The method of claim 1, wherein:
the imaging device is configured to acquire and update the first image of the surgical site in real time;
the memory of the computer system includes a tracking module, the tracking module configured to determine a track of the surgical instrument using the first image; and
the registration module further configured to generate the augmented reality depiction of the surgical site including a predetermined approach of the surgical instrument to the surgical site based upon the track of the surgical instrument determined using the first image by the tracking module.

12. The method of claim 11, wherein the augmented reality depiction identifies whether the track of the surgical instrument matches the predetermined approach.

13. The method of claim 1, wherein the memory of the computer system includes a modification module, the modification module configured to modify the predetermined surgical plan.

14. The method of claim 13, wherein the display device is further configured to display an augmented reality depiction including a control panel configured to respond to a gesture of the operator to communicate with the modification module and allow the operator to modify the predetermined surgical plan.

15. The method of claim 13, wherein the computer system is in communication with a remote system, the remote system configured to access the modification module, thereby allowing a remote operator to modify the predetermined surgical plan.

16. The method of claim 1, wherein preparing, by the operator, the portion of the surgical site using the surgical instrument guided by the augmented reality depiction to form the prepared site includes removal of bone.

17. The method of claim 1:
wherein:
the imaging device is configured to acquire and update the first image of the surgical site in real time;
the memory of the computer system includes an image module, the image module including a preexisting image of the surgical site, and the registration module is configured to correlate the predetermined surgical plan with the first image and the preexisting image to generate the augmented reality depiction of the surgical site using the first image, and the first image includes a portion of the surgical site viewable by the operator and the preexisting image includes a portion of the surgical site not viewable by the operator;
the memory of the computer system includes a predictive module, the predictive module configured to correlate a predictive image based upon the predetermined surgical plan with the first image to generate the augmented reality depiction of the surgical site using the first image, the predictive module matches one or more anatomical landmarks from the first image with the predetermined surgical plan to position the predictive image in correlating the predictive image and the first image to generate the augmented reality depiction of the surgical site using the first image;

the memory of the computer system includes a positioning module, the positioning module configured to correlate the positioned implant at the prepared site with the predetermined surgical plan and determine an implant deviation;

the memory of the computer system includes a tracking module, the tracking module configured to determine a track of the surgical instrument using the first image, wherein the registration module is further configured to generate the augmented reality depiction of the surgical site including a predetermined approach of the surgical instrument to the surgical site based upon the track of the surgical instrument determined using the first image by the tracking module, and the augmented reality depiction identifies whether the track of the surgical instrument matches the predetermined approach; and the memory of the computer system includes a modification module, the modification module configured to modify the predetermined surgical plan, the display device is further configured to display an augmented reality depiction including a control panel configured to respond to a gesture of the operator to communicate with the modification module and allow the operator to modify the predetermined surgical plan, and the computer system is in communication with a remote system, the remote system configured to access the modification module, thereby allowing a remote operator to modify the predetermined surgical plan;

further comprising:

moving, by the operator, a portion of the surgical site of the patient, wherein, the imaging device acquires and updates the first image of a moved portion of the surgical site in real time;

preparing, by the operator, the portion of the surgical site using the surgical instrument guided by the augmented reality depiction to form the prepared site includes revealing one or more additional anatomical landmarks at the surgical site, wherein the predictive module matches the one or more additional anatomical landmarks from the first image with the predetermined surgical plan to position or reposition the predictive image in correlating the predictive image and the first image to generate the augmented reality depiction of the surgical site using the first image;

adjusting, by the operator, the positioned implant to account for the implant deviation to form a repositioned implant; and preparing, by the operator, the portion of the surgical site using the surgical instrument guided by the augmented reality depiction to form the prepared site includes removal of bone.

18. An augmented reality system for performing arthroplasty on a surgical site of a patient by an operator, comprising:

an imaging device including a camera and configured to acquire and update a first image of the surgical site in real time including acquiring an image of an anatomical landmark;

a display device configured to display an augmented reality depiction of the surgical site; and a computer system having a processor and a memory, the computer system in communication with the imaging device and the display device, the memory including:

a registration module configured to correlate a predetermined surgical plan with the first image including identifying the anatomical landmark to generate the augmented reality depiction of the surgical site using the first image;

an image module, the image module including a preexisting image of the surgical site, and the registration module is configured to correlate the predetermined surgical plan with the first image and the preexisting image to generate the augmented reality depiction of the surgical site using the first image;

a predictive module, the predictive module configured to correlate a predictive image based upon the predetermined surgical plan with the first image to generate the augmented reality depiction of the surgical site using the first image;

a positioning module, the positioning module configured to correlate a positioned implant at a prepared site with the predetermined surgical plan and determine an implant deviation;

a tracking module, the tracking module configured to determine a track of a surgical instrument using the first image, the registration module further configured to generate the augmented reality depiction of the surgical site including a predetermined approach of the surgical instrument to the surgical site based upon the track of the surgical instrument determined using the first image by the tracking module; and a modification module, the modification module configured to modify the predetermined surgical plan, wherein the display device is further configured to display an augmented reality depiction including a control panel configured to respond to a gesture of the operator to communicate with the modification module and allow the operator to modify the predetermined surgical plan, and the computer system is in communication with a remote system, the remote system configured to access the modification module, thereby allowing a remote operator to modify the predetermined surgical plan.

19. The augmented reality system of claim 18, wherein:

the first image includes a portion of the surgical site viewable by the operator and the preexisting image includes a portion of the surgical site not viewable by the operator;

the predictive module matches one or more anatomical landmarks from the first image with the predetermined surgical plan to position the predictive image in correlating the predictive image and the first image to generate the augmented reality depiction of the surgical site using the first image; and the predictive module matches the one or more anatomical landmarks from the first image with the predetermined surgical plan to position or reposition the predictive image in correlating the predictive image and the first image to generate the augmented reality depiction of the surgical site using the first image.

20. The method of claim 1, wherein:

the registration module is configured to:

perform intraoperative registration by identifying a bone or a soft tissue landmark and generate an image based on the identified landmark, or use artificial intelligence to create an image from an anatomy atlas based on the identified landmark, wherein the augmented reality depiction of the surgical site is generated using the image created by the registration module.

\* \* \* \* \*